US008632813B2

(12) United States Patent
Wen et al.

(10) Patent No.: US 8,632,813 B2
(45) Date of Patent: Jan. 21, 2014

(54) PROSTAGLANDIN COMPOSITIONS AND METHODS FOR THE TREATMENT OF VASOSPASM

(75) Inventors: Tian Wen, Beijing (CN); Liu Liu, Beijing (CN); Mingqi Lu, Lawrenceville, NJ (US); Jieshan Bai, Beijing (CN); Y. Joseph Mo, Princeton, NJ (US)

(73) Assignee: Nexmed (Holdings), Inc., San Diego, CA (US)

( * ) Notice: Subject to any disclaimer, the term of this patent is extended or adjusted under 35 U.S.C. 154(b) by 1428 days.

(21) Appl. No.: 11/875,725

(22) Filed: Oct. 19, 2007

(65) Prior Publication Data

US 2008/0069883 A1  Mar. 20, 2008

Related U.S. Application Data

(62) Division of application No. 10/815,119, filed on Mar. 31, 2004, now abandoned.

(60) Provisional application No. 60/459,896, filed on Apr. 2, 2003.

(51) Int. Cl.
*A61K 9/14* (2006.01)
*A61K 31/5575* (2006.01)
*A61K 31/715* (2006.01)
*A61K 47/00* (2006.01)
*A61F 2/00* (2006.01)

(52) U.S. Cl.
USPC ........... 424/488; 514/573; 514/947; 514/782; 514/54; 424/428

(58) Field of Classification Search
USPC ............ 424/428, 487, 423, 488; 514/573, 54, 514/947, 782
See application file for complete search history.

(56) References Cited

U.S. PATENT DOCUMENTS

| | | | |
|---|---|---|---|
| 4,029,814 A | 6/1977 | Bundy | |
| 4,212,987 A | 7/1980 | Axen | |
| 4,311,707 A | 1/1982 | Birnbaum et al. | |
| 4,820,732 A | 4/1989 | Shell et al. | |
| 4,955,878 A | 9/1990 | See et al. | |
| 4,980,378 A | 12/1990 | Wong et al. | |
| 5,082,866 A | 1/1992 | Wong et al. | |
| 5,252,605 A | 10/1993 | Veno | |
| 5,403,867 A | 4/1995 | Okumura et al. | |
| 6,046,244 A * | 4/2000 | Buyuktimkin et al. | 514/785 |
| 6,118,020 A | 9/2000 | Buyuktimkin et al. | |
| 6,323,241 B1 | 11/2001 | Yeager et al. | |
| 6,414,028 B1 | 7/2002 | Buyuktimkin et al. | |
| 6,489,207 B2 | 12/2002 | Furukawa et al. | |
| 2006/0148907 A1 * | 7/2006 | Nicholson et al. | 514/729 |

FOREIGN PATENT DOCUMENTS

| | | | |
|---|---|---|---|
| CA | 2 442 479 | A | 11/2000 |
| EP | 0 292643 | A | 11/1988 |
| EP | 0 503 887 | A2 | 9/1992 |
| WO | WO 95/09590 | | 4/1995 |
| WO | WO 99/22714 | A | 5/1999 |

OTHER PUBLICATIONS

Clifford in the "Treatment of vasospastic disease with prostaglandin E1," in Br Med J. Oct. 18, 1980; 281(6247): 1031-1034.*
Verma et al. "Fundamnentals of Reperfusion Injury for the Clinical Cardiologist," in Journal of the American Heart Associatio, 2002:105, 2332-2336.*
Buncke, H.J., "Microsurgery: Transplantation-Replantation", on-line edition, chapter 36, http://buncke.org/textbook.html, accessed Dec. 13, 2002.
Büyüktimkin, N., et al., "*Chemical Means of Transdermal Drug Permeation Enhancement.*" In *Transdermal and Topical Drug Delivery Systems*, Tapash K. Ghosh et al., eds. (IL: Interpharm Press), pp. 357-475 (1997).
Cragg, A., et al., "Vessel wall arachidonate metabolism after angioplasty", *Am J Cardiol* 51:1441-45 (1983).
Mizushima, Y., et al., "Prostaglandin E1 is more effective, when incorporated in lipid microspheres, for treatment of peripheral vascular diseases in man," Journal of Pharmacology 1983 vol. 35, No. 10, 1983, pp. 666-667.
Sakai, Y., et al., "Prostaglandin E2 regulates the expression of basic fibroblast growth factor messenger RNA in normal human fibroblasts," *Kobe J. Med. Sci.* 47:35-45 (2001).
Slodicke, R., et al. "Die Anwendung von Prostaglandin $E_1$ bei milcrovaskulären Rekonstruktion der oberen Extremität nach Akuttraumen, (Using Prostaglandin $E_1$ in microvascular reconstruction of the upper extremity after acute trauma)," *Unfallchirurg*, Jan.; 105(1): 14-8 (2002). (English abstract on p. 15).
Smalling, Richard W. et al., "Infarct salvage with liposomal prostaglandin E-1 administered by intravenous bolus immediately before reperfusion in a canine infarction-reperfusion model," Circulation, vol. 92, No. 4, 1995, pp. 935-943.
Zollikofer, C.L., et al., "Prostaglandins and angioplasty. An experimental study in canine arteries," *Radiology*, 149(3): 681-5 (1983).
Sawada Y., et al., A new system of treating wounds by a continuous topical application of medication. Br J Plast Surg. Jan. 1990; 43(1): 83-7.
Sawada Y. et al. A study of topical and systemic prostaglandin E1 and survival of experimental skin flaps. Br J Plast Surg. Dec. 1993;46(8):670-2.
Nakanishi Y, et al. The transepidermal absorption of prostaglandin E1 as a topical ointment: an experimental study of application over a rat skin flap. Ann Plast Surg. Jan. 1998; 40(1):44-7.
Eskitascioglu T, et al. The effects of topical prostacyclin and prostaglandin E1 on flap survival after nicotine application in rats. Ann Plast Surg. Aug. 2005;55(2):202-6.
Kuwahara H, et al. The effects of lipo-prostaglandin E1 on axial pattern flaps in rabbits. Ann Plast Surg. Dec. 1995;35(6):620-6.

(Continued)

*Primary Examiner* — Blessing M Fubara
(74) *Attorney, Agent, or Firm* — Foley & Lardner LLP

(57) ABSTRACT

Compositions and methods for the treatment of vasospasm are provided comprising applying an amount of a semi-solid vasoactive prostaglandin composition to the affected tissue. Also provided are methods of improving microcirculation in a replanted body part.

13 Claims, 5 Drawing Sheets

(56) References Cited

OTHER PUBLICATIONS

Hong JP, et al. The effect of prostaglandin E1 versus ischemia-reperfusion injury of musculocutaneous flaps. Ann Plast Surg. Sep. 2001;47(3):316-21.

"Peripheral vascular disease" in Online Medical Dictionary at //cancerweb.ncl.ac.uk/cgi-bin/omd?query=peripheral+vascular+disease. 1997-200.

"Peripheral Arterial Disease" in Merck Manual of Medical Information—Second Home Edition Online Edition.at www.merck.com/mmpe/sec07/ch080/ch080f._2004-2008.

"Raynaud's Phenomenon" in Merck Manual of Medical Information—Second Home Edition Online Edition.at www.merck.com/mmpe/sec07/ch080/ch080g. 2004-2008.

"Acrocyanosis" in Merck Manual of Medical Information—Second Home Edition Online Edition.at www.merck.com/mmpe/sec07/ch080b._2004-2008.

"Vasospasm" in Online Medical Dictionary at //cancerweb.ncl.ac.uk/cgi-bin/omd?query=vasospasm. 1997-2007.

Definition of "replantation," p. 1445, Dorland's Illustrated Medical Dictionary, 28 Ed., W. B. Saunders Co., Philadelphia 1994.

Coffman, J.D., Raynaud's phenomenon. An update, Hypertension 1991, 17:593-602.

Guyatt, G.H., et al., Evidence Based Medicine. A New Approach to Teaching the Practice of Medicine, JAMA, 268(17), Nov. 4, 1992 pp. 2420-2415.

Guyatt, G.H., Sackett, D.L., Cook, D.J., Users' Guides to the Medical Literature. II. How to Use an Article About Therapy or Prevention. A. Are the Results of the Study Valid?, JAMA, 270(21), Dec. 1, 1993, pp. 2598-2601.

Guyatt, G.H., Sackett, D.L., Cook, D.J., Users' Guides to the Medical Literature. II. How to Use an Article About Therapy or Prevention. B. What Are the Results and Will They Help Me in Caring for My Patients?, JAMA, 270(21), Jan. 5, 1994, pp. 59-63.

Mohrland, J.S., Porter, J.M., Smith, E.A., Belch, J., Simms, M.H., A multiclinic, placebo-controlled, double-blind study of prostaglandin E1 in Raynaud's syndrome, Annals of the Rheumatic Diseases, 1985; 44, 754-760.

Oxford-Centre for Evidence-Based Medicine, "Levels of Evidence and Grades of Recommendation," web page archived on Jun. 21, 2003, retrieved from the Internet Archive WayBack Machine on Apr. 22, 2012, http://web.archive.org/web/20030621165628/http://www.cebm.net/levels_of_evidence.asp[Apr. 22, 2012 3:30:14 PM].

Oxman, A.D., Sackett, D.L., Guyatt, G.H., Users' Guides to the Medical Literature. I. How to Get Started, JAMA, 270(17), Nov. 3, 1993, pp. 2093-2095.

Pope, S., Fenlon, D., Thompson, A., Shea, B., Furst, D., Wells, G., Silman, A., Iloprost and cisaprost for Raynaud's phenomenon in progressive systemic sclerosis, Cochrane Database Syst Rev. 1998, Issue 2. Art. No. CD000953. Reprinted in 2009 and published by John Wiley & Sons, Ltd.

* cited by examiner

PROSTAGLANDIN COMPOSITIONS AND METHODS FOR THE TREATMENT OF VASOSPASM

CROSS REFERENCES TO RELATED APPLICATIONS

The present application is a divisional application and claims the benefit of copending U.S. patent application Ser. No. 10/815,119, filed Mar. 31, 2004, which claims the benefit of U.S. Provisional Application No. 60/459,896, filed Apr. 2, 2003. The entire contents of each of the above applications are incorporated herein by reference in their entirety.

BACKGROUND OF THE INVENTION

Vasospasm is a constriction of blood vessels, resulting in ischemia of the tissue supplied by the blood vessels. Prolonged spasm in arteries, veins, and vein grafts has been described as a physiologic complication in microsurgery for over 20 years (Buncke, H. J, Microsurgery: Transplantation-Replantation, on-line edition, Chapter 36). Vasospasm results from several processes including intrinsic smooth muscle contraction, local noradrenaline metabolism, neurogenic and hormonal processes, and prostaglandin metabolism. Topical agents, such as magnesium sulfate, lidocaine, papaverine and chlorpromazine have been reported to successfully relieve vasospasm. Other described methods for relieving vasospasm include nerve blocks, systemic adrenergic agents and systemic vasodilating agents such as sodium nitroprusside. Id at page 2. Experimental attempts to find roles for modifiers of prostaglandin function, sympatholytics, calcium channel blockers and numerous other drugs have generally not succeeded in producing either clearly applicable models or reproducibly positive results. Id at page 5. Vasospasm may be elicited by cold, mechanical trauma or chemical mediators, including adrenalin.

If circulation is not re-established in time, tissue damage may result due to reperfusion injury. Reperfusion injury refers to the cellular changes and tissue damage seen after a period of total ischemia followed by reperfusion. Extremity replantation, organ transplantation, free flap tissue reconstruction and even myocardial infarction and stroke are all clinical examples of interval tissue ischemia which can lead to tissue loss due to reperfusion injury after blood flow is re-established. Tissue reperfusion injury, seen in its full clinical extent as the no-reflow phenomenon, appears as inflammatory response to reperfusion, resulting in the ultimate death of the tissue.

Prostaglandin $E_1$ is a derivative of prostanoic acid, a 20-carbon atom lipid acid, represented by the formula:

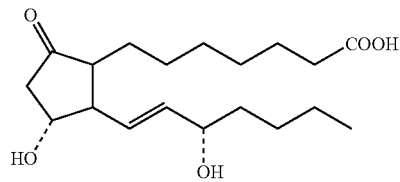 [SMILES: CCCC[C@H](O)/C=C/C1C(CCCCCCC(=O)O)C(=O)C[C@H]1O]

and is commercially available, e.g., from Chinoin Pharmaceutical and Chemical Works Ltd. (Budapest, Hungary) under the designation "Alprostadil USP," from Pharmacia & Upjohn under the designation "Caverject". Prostaglandin $E_1$ complexed with alpha-cyclodextrin is available as alprostatil alfadex from Ono Pharmaceuticals (Japan) and in an injectable form under the designation "Edex®" or "Viradex®" from Schwarz Pharma (Germany).

Prostaglandin $E_1$ is a vasodilator useful to maintain open blood vessels and, therefore, to treat peripheral vascular disease among other ailments. While the potential benefits from transdermal delivery of prostaglandin $E_1$ have long been recognized, prior efforts at developing a topical composition for prostaglandin delivery have not been fully successful. Working alone, most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not adversely affect the physical qualities of the available dosage forms (e.g., cream or gel), or the cosmetic quality of the topical composition.

A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Büyüktimkin et al., Chemical Means of Transdermal Drug Permeation Enhancement in *Transdermal and Topical Drug Delivery Systems*, Gosh T. K., Pfister W. R., Yum S. I. (Eds.), Interpharm Press Inc., Buffalo Grove, Ill. (1997).

SUMMARY OF THE INVENTION

We have found that administration of prostaglandin compositions comprising a penetration enhancer relieves constriction of a blood vessel in vasospasm and restores blood flow. The method and compositions are useful for the relief of vasospasm in several conditions, including vasospasm occurring during and following replantation surgery. In other aspects, the invention provides methods and compositions for improving microcirculation in a replanted body part. In other embodiments, the present invention provides methods of treating tissue ischemia. In further preferred embodiments, the present invention provides compositions and methods for preventing reperfusion injury.

In one embodiment, the invention provides a method of treating vasospasm in a subject needing such treatment comprising the steps of applying an effective amount of a semisolid prostaglandin composition to the region of the subject's tissue requiring treatment, the composition comprising a vasoactive prostaglandin; a polymeric thickener selected from the group consisting of a polysaccharide gum and a polyacrylic acid polymer; a lipophilic component that is selected from the group consisting of an aliphatic $C_1$ to $C_8$ alcohol, an aliphatic $C_8$ to $C_{30}$ ester and mixtures thereof; water and a buffer system that provides a buffered pH value for the composition in the range of about 3 to about 7.4. In particularly preferred embodiments, the composition further comprises a penetration enhancer. In preferred embodiments, the present invention provides a composition comprising an effective amount of a vasoactive prostaglandin; a penetration enhancer selected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof; a polymer thickener selected from the group consisting of a polyacrylic acid polymer, a polysaccharide gum, a modified polysaccharide gum and mixtures thereof; a lipophilic component; water and a buffer system, wherein the pH of the composition is 3 to 7.4. The composition may be applied topically to the skin, parenterally (e.g., subcutaneously) or directly to exposed tissues such as the vascular extima of blood vessels during surgery or wound treatment.

The vasoactive prostaglandin is suitably selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, a pharmaceutically acceptable salt thereof, a lower alkyl ester thereof and a mixture thereof. Preferably, the vasoactive prostaglandin is selected from the group consisting of prostaglandin $E_1$, prostaglandin $E_2$, a pharmaceutically acceptable salt thereof, a lower alkyl ester thereof and a mixture thereof. In preferred embodiments, the vasoactive prostaglandin is $PGE_1$. If the vasoactive prostaglandin is $PGE_1$, the dose per application is suitably at least about 0.08 mg $PGE_1$, preferably about 0.08 mg to about 0.64 mg $PGE_1$.

In some preferred embodiments, the composition exhibits non-Newtonian rheological properties, suitably comprising a shear-thinning polysaccharide gum or a shear-thinning polyacrylic acid polymer. In one embodiment, the composition is thixotropic. In another embodiment, the composition is pseudoplastic. In preferred embodiments, the composition has a viscosity of about 5,000 centipoise (cps) to about 20,000 cps, more preferably from about 7,000 cps to about 13,000 cps.

In preferred embodiments, the shear-thinning polysaccharide gum is a galactomannan gum or a modified galactomannan gum. A preferred modified galactomannan gum is a modified guar gum. In one embodiment, the penetration enhancer is dodecyl 2-(N,N-dimethylamino)-propionate or a pharmaceutically acceptable salt thereof. In another embodiment, the penetration enhancer comprises a mixture of lauric acid, isopropyl myristate and triethanolamine. In one embodiment, the lipophilic component comprises at least one aliphatic $C_8$ to $C_{30}$ ester. In a preferred embodiment, the lipophilic component comprises at least one glyceryl ester selected from the group consisting of monoglycerides, diglycerides, triglycerides, and mixtures thereof. In another embodiment, the lipophilic component comprises at least one glyceryl ester selected from the group consisting of glyceryl monooleate, triolein, trimyristin, tristearin, and mixtures thereof.

Typically, the acidic buffer system provides a buffered pH value for said composition in the range of about 3 to about 7.4, more preferably about 3.0 to about 6.5, most preferably from about 3.5 to about 6.0. In certain embodiments the composition further comprises an emulsifier selected from the group consisting of sucrose esters, polyoxyethylene sorbitan esters, long chain alcohols, and glyceryl esters. Suitably, the emulsifier comprises at least one glyceryl ester selected from the group consisting of glyceryl monooleate, triolein, trimyristin, tristearin, and mixtures thereof. Optionally, the composition further comprises a fragrance. In some embodiments the composition further comprises up to about 5 percent myrtenol, based on the total weight of the composition. Suitably, the composition further comprises a preservative. In other embodiments, the composition further comprises a topical anesthetic.

In preferred embodiments, the present invention provides a method of preventing reperfusion injury of ischemic tissue by providing a composition of the present invention, applying the composition to the surface of the affected tissue, and optionally, applying the composition to the vascular extima of blood vessels supplying the affected tissue. In preferred embodiments, the vascular perfusion volume to the tissue returns to normal within 30 minutes, more preferably in 10 minutes, optimally less than 10 minutes after the application of the composition. In other aspects, the present invention provides a composition useful in the manufacture of a medicament for the treatment of vasospasm, for improving local microcirculation, especially in a replanted body part, or for preventing reperfusion injury.

Other and further aims, purposes, features, advantages, embodiments and the like will be apparent to those skilled in the art from the present specification and the appended claims.

DETAILED DESCRIPTION OF THE INVENTION

Figure 1A:
FIG. 1 shows images of the transilluminated shaved dorsal surfaces of the right (FIG. 1A) and left ears (FIG. 1B) of a rabbit. The two arrows in each Fig. indicate the vasospasm that was observed 5 minutes after injections of 2 ml of a 0.1% adrenaline solution into the tissue next to the central arteries and veins near the base of both ears.

Vasospasm is a recognized problem that limits the success of replantation of body parts such as fingers, arms and legs. Even if microsurgery is performed to reconnect severed blood vessels, vasospasm can impair the surgeon's ability to suture during surgery, and can block post-surgery blood flow to the reattached limb. When the vasospasm occurs before the microsurgery, the blood vessels can be so rigid that the surgeon is unable to perform the anastomosis. If the vasospasm occurs after the microsurgery, the blood vessel on one side of the anastomosis could get so rigid that blood flow was blocked.

Current treatment with vasodilators has a success rate around 20%, and effects are not seen for 30-60 minutes or longer. If the treatment with current therapy is a failure, tissue damage due to ischemia beyond the region of vasospasm causes the loss of the reattached limb. In such cases, the surgeon must amputate the limb, causing additional suffering to the subject, and involving additional expense and hospitalization time.

In general, treatment with the methods and topical prostaglandin compositions of the present invention produced an increase in blood flow through the region of vasospasm within about five minutes. The treatment has a high success rate in early clinical studies, approaching 100% effectiveness. In these studies, the subjects were patients who were treated and studied at Beijing Jishuitan Hospital. Arms, legs or fingers of the patients, generally severed because of automobile or factory accidents, were reattached (replantation) involving microsurgery for arterial anastomosis.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

"Alkyl" means the monovalent linear or branched saturated hydrocarbon radical, consisting solely of carbon and hydrogen atoms, having from one to twenty carbon atoms inclusive, unless otherwise indicated. Examples of an alkyl radical include, but are not limited to, methyl, ethyl, propyl, isopropyl, isobutyl, sec-butyl, tert-butyl, pentyl, n-hexyl, octyl, dodecyl, tetradecyl, eicosyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of a lower alkyl radical include, but are not limited to, methyl, ethyl, propyl, isopropyl, tert-butyl, n-butyl, n-hexyl, and the like.

"Lower alkoxy" means the radical —O—R, wherein R is a lower alkyl radical as defined above. Examples of a lower alkoxy radical include, but are not limited to, methoxy, ethoxy, isopropoxy, and the like.

"Halogen" means the radical fluoro, bromo, chloro, and/or iodo.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" of a compound means a salt that is pharmaceutically acceptable, as defined above, and that possesses the desired pharmacological activity of the parent compound. Such salts include:

1. acid addition salts formed with inorganic acids such as hydrochloric acid, hydrobromic acid, hydrofluoric acid, hydroiodic acid, trifluoroacetic acid, sulfuric acid, nitric acid, phosphoric acid, boric acid and the like; or formed with organic acids such as acetic acid, benzenesulfonic acid, benzoic acid, camphorsulfonic acid, p-chlorobenzenesulfonic acid, cinnamic acid, citric acid, cylcopentanepropionic acid, ethanesulfonic acid, 1,2-ethanedisulfonic acid, formic acid, fumaric acid, glucoheptonic acid, gluconic acid, glutamic acid, glycolic acid, hexanoic acid, heptanoic acid, o-(hydroxybenzoyl)benzoic acid, hydroxynaphtoic acid, 2-hydroxyethanesulfonic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trifluoromethanesulfonic acid, trimethylacetic acid, and the like; or 2. salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, methylamine, ethylamine, hydroxyethylamine, propylamine, dimethylamine, diethylamine, trimethylamine, triethylamine, ethylenediamine, hydroethylamine, morpholine, piperazine, and guanidine and the like. Acceptable inorganic bases include aluminum hydroxide, ammonium hydroxide, calcium hydroxide, potassium hydroxide, sodium carbonate, sodium hydroxide and hydrazine. The preferred pharmaceutically acceptable salts are the salts formed from hydrochloric acid, and trifluoroacetic acid.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgement of the attending medical or veterinary practitioner, and other factors.

The term "pharmacological effect" as used herein encompasses effects produced in the subject that achieve the intended purpose of a therapy. In one preferred embodiment, a pharmacological effect means that vasospasm symptoms of the subject being treated are prevented, alleviated, or reduced. For example, a pharmacological effect would be one that results in the prevention or reduction of vasospasm in a treated subject.

"Disease state" means any disease, condition, symptom, or indication.

"Treating" or "treatment" of a disease state includes:

1. preventing the disease state, i.e. causing the clinical symptoms of the disease state not to develop in a subject that may be exposed to or predisposed to the disease state, but does not yet experience or display symptoms of the disease state, 2. inhibiting the disease state, i.e., arresting the development of the disease state or its clinical symptoms, or 3. relieving the disease state, i.e., causing temporary or progressive regression of the disease state or its clinical symptoms.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

In a preferred embodiment, the pharmaceutical composition comprises at least one vasoactive prostaglandin, preferably prostaglandin $E_1$, a penetration enhancer, a polymeric thickener, a lipophilic component, water and a buffer system that provides a buffered pH value for said composition in the range of about 3 to about 7.4. In one preferred embodiment, the penetration enhancer is an alkyl (N-substituted amino) ester or a pharmaceutically acceptable salt thereof.

Vasoactive prostaglandins are those that act as peripheral vasodilators, including naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost. Prostaglandin $E_1$ and prostaglandin $E_2$ are particularly preferred vasoactive prostaglandins for use in conjunction with the present method.

Additionally, simultaneous administration of one or more non-ecosanoid vasodilators may be desirable and may in some cases exhibit a synergistic effect. The combination of prazosin with prostaglandin $E_1$ has been found to be particularly advantageous in this regard.

Suitable non-ecosanoid vasodilators include, but are not limited to: nitrates such as nitroglycerin, isosorbide dinitrate, erythrityl tetranitrate, amyl nitrate, sodium nitroprusside, molsidornine, linsidomine chlorhydrate ("SIN-1") and S-nitroso-N-acetyl-d,l-penicillamine ("SNAP"); amino acids such as L-arginine; long and short acting α-adrenergic blockers such as phenoxybenzaamine, dibenamine, phentolamine, tamsulosin and indoramin, especially quinazoline derivatives such as alfuzosin, bunazosin, doxazosin, terazosin, prazosin, and trimazosin; vasodilative natural herbal compositions and bioactive extracts thereof, such as gosyajinki-gan, *Satureia obovata*, bai-hua qian-hu, lipotab, saiboku-to, vinpocetine, *Gingko biloba*, bacopa, *Gynostemma pentaphyllum*, gypenosides, *Evodia rutaecarpa*, rutaecarpine, dehydroevodiamine, danshen, salviae miltiorrhizae radix, shosaikoto, *Zizyphi fructus*, ginseng and mixtures thereof (U.S. Pat. No. 6,007,824); ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone and vasoactive intestinal peptides.

Prostaglandin $E_1$ is well known to those skilled in the art. Reference may be had to various literature references for its pharmacological activities, side effects, and normal dosage ranges. See for example, *Physician's Desk Reference*, 51st Ed. (1997), *The Merck Index*, 12th Ed., Merck & Co., N.J. (1996), and *Martindale The Extra Pharmacopoeia*, 28th Ed., London, The Pharmaceutical Press (1982). Prostaglandin $E_1$ as well as other compounds referenced herein are intended to encompass pharmaceutically acceptable derivatives including physiologically compatible salts and ester derivatives thereof.

The quantity of vasoactive prostaglandin, such as prostaglandin $E_1$, in the pharmaceutical composition is a therapeutically effective amount and necessarily varies according to the desired dose, the dosage form (e.g., suppository or topical), and the particular form of vasoactive prostaglandin used. The term "prostaglandin" as used generically herein refers to the prostaglandin free acid and pharmaceutically acceptable derivatives thereof, including, for example $PGE_1$, pharmaceutically acceptable salts and lower alkyl esters thereof (the term "lower alkyl" as used herein means straight chain or branched chain alkyl containing one to four carbon atoms). The composition generally contains between 0.001 percent to 1 percent of vasoactive prostaglandin, e.g., prostaglandin $E_1$, typically contains between 0.05 percent to 1 percent, preferably from 0.1 percent to 0.5 percent, based on the total weight of the composition.

When used in combination with a vasoactive prostaglandin, a piperazinyl quinazoline antihypertensive, such as prazosin, is present in the amount of about 0.1 mg to about 2.0 mg per unit dose, depending on the potency of the particular piperazinyl quinazoline antihypertensive and the type and dose of vasoactive prostaglandin used. The dose and the proportion of vasoactive prostaglandin and the piperazinyl quinazoline antihypertensive can be routinely determined by one of ordinary skill without undo experimentation.

Working alone, most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not adversely affect the physical qualities of the available dosage forms (e.g. cream or gel), or the cosmetic quality of the topical composition.

A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Büyüktimkin et al., Chemical Means of Transdermal Drug Permeation Enhancement in *Transdermal and Topical Drug Delivery Systems*, Gosh T. K., Pfister W. R., Yum S. I. (Eds.), Interpharm Press Inc., Buffalo Grove, Ill. (1997). Suitable penetration enhancers for use in prostaglandin topical compositions are disclosed in U.S. Pat. Nos. 4,980,378, 5,082,866 and 6,118,020, and published international patent application WO 95/09590. Topical compositions employing such penetration enhancers for the delivery of prostaglandins are disclosed in U.S. Pat. Nos. 6,046,244, 6,323,241, 6,414,028, and 6,489,207.

The topical composition of the present invention can contain one or more penetration enhancers. Among the preferred penetration enhancers for the present invention are ethanol, propylene glycol, glycerol, ethyl laurate, triethanolamine, isopropyl palmitate, isopropyl myristate, lauric acid, laurocapram (Azone™), dioxolanes (described in U.S. Pat. No. 4,861,764), macrocyclic ketones, HP-101, oxazolidones and biodegradable penetration enhancers (described in U.S. Pat. Nos. 4,980,378 and 5,082,866 to Wong et al. such as alkyl-2-(N,N-disubstituted amino)alkanoates (e.g., dodecyl N,N-dimethylamino isoproprionate (DDAIP)), N,N-disubstituted amino alkanol alkanoates (WO 95/09590) and mixtures thereof. When present, isopropyl myristate is present in the amount of about 0.1 to about 10 weight percent, preferably about 3 weight percent. When present, triethanolamine is present in the amount of about 0.1 to about 5 weight percent, preferably about 0.5 weight percent. When present, lauric acid is present in the amount of about 0.1 to about 5 weight percent, preferably about 1 weight percent.

The penetration enhancer is present in an amount sufficient to enhance the penetration of the vasoactive prostaglandin, e.g., prostaglandin $E_1$. The specific amount varies necessarily according to the desired release rate and the specific form of prostaglandin $E_1$ used. Generally, the penetration enhancer is present in an amount ranging from about 0.5 weight percent to about 20 weight percent, based on the total weight of the composition. Preferably, the penetration enhancer is present in an amount ranging from about 1 weight percent to about 10 weight percent of the composition. More preferably, the penetration enhancer is present in an amount ranging from about 1 weight percent to about 5 weight percent of the composition.

In general, suitable penetration enhancers can be chosen from those listed above as well as sulfoxides, alcohols, fatty acids, fatty acid esters, polyols, amides, surfactants, terpenes, alkanones, organic acids and mixtures thereof. See generally Chattaraj, S. C. and Walker, R. B., Penetration Enhancer Classification, pp. 5-20 in Maibach, H. I., and Smith, H. E., (eds.), *Percutaneous Penetration Enhancers*, CRC Press, Inc., Boca Raton, Fla. (1995) and Büyüktimkin, N., et al., Chemical Means of Transdermal Drug Permeation Enhancement, in Gosh, T. K., et al., (eds.) *Transdermal and Topical Drug Delivery Systems*, Interpharm Press, Inc., Buffalo Grove, Ill. (1997). Suitable sulfoxides include dimethylsulfoxide, decylmethylsulfoxide and mixtures thereof. Suitable alcohols include ethanol, propanol, butanol, pentanol, hexanol, octanol, nonanol, decanol, 2-butanol, 2-pentanol, benzyl alcohol, caprylic alcohol, decyl alcohol, lauryl alcohol, 2-lauryl alcohol, myristyl alcohol, cetyl alcohol, stearyl alcohol, oleyl alcohol, linolyl alcohol, linolenyl alcohol and mixtures thereof. Suitable fatty acids include valeric, heptanoic, pelargonic, caproic, capric, lauric, myristic, stearic, oleic, linoleic, linolenic, caprylic, isovaleric, neopentanoic, neoheptanoic, neononanoic, trimethyl hexanoic, neodecanoic and isostearic acids and mixtures thereof.

Suitable fatty acid esters include isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate, ethyl oleate, ethyl laurate and mixtures thereof. Suitable polyols include propylene glycol, polyethylene glycol, ethylene glycol, diethylene glycol, triethylene glycol, dipropylene glycol, glycerol, propanediol, sorbitol, dextrans, butanediol, pentanediol, hexanetriol and mixtures thereof.

Suitable amides include urea, dimethylacetamide, diethyltoluamide, dimethylformamide, dimethyloctamide, dimethyldecamide, 1-alkyl-4-imidazolin-2-one, pyrrolidone derivatives, cyclic amides, hexamethylenelauramide and its derivatives, diethanolamine, triethanolamine and mixtures thereof. Suitable pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-decyl-thioethyl-2-pyrrolidone (HP-101), 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkypyrrolidone, fatty acid esters of N-(2-hydroxymethyl)-2-pyrrolidone and mixtures thereof. Suitable cyclic amides include 1-dodecylazacycloheptane-2-one (laurocapram, Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyloctyl)azacycloheptan-2-one, 1-geranylazacyclohexane-2-one, 1-geranylazacyclopentan-2,5-dione, 1-farnesylazacyclopentan-2-one and mixtures thereof.

Suitable surfactants include anionic surfactants, cationic surfactants, nonionic surfactants, bile salts and lecithin. Suitable anionic surfactants include sodium laurate, sodium lauryl sulfate and mixtures thereof. Suitable cationic surfactants include cetyltrimethylammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, and mixtures thereof. Suitable nonionic surfactants include α-hydro-ω-hydroxy-poly(oxyethylene)-poly(oxypropyl)poly(oxyethylene)block copolymers, polyoxyethylene ethers, polyoxyethylene sorbitan esters, polyethylene glycol esters of fatty alcohols and mixtures thereof. Suitable α-hydro-ω-hydroxy-poly(oxyethylene) poly(oxypropyl)poly(oxyethylene)block copolymers include Poloxamers 231, 182, and 184 and mixtures thereof. Suitable polyoxyethylene ethers include 4-lauryl ether (Brij 30), (Brij 93), (Brij 96), 20-oleyl ether (Brij 99) and mixtures thereof. Suitable polyoxyethylene sorbitan esters include the monolaurate (Tween 20, Span 20) the monopalmitate (Tween 40), the monostearate (Tween 60), and the monooleate (Tween 80) and mixtures thereof. Suitable polyethylene glycol esters of fatty acids include the 8-oxyethylene stearate ester (Myrj 45), (Myrj 51), the 40-oxyethylene stearate ester (Myrj 52) and mixtures thereof. Suitable bile salts include sodium cholate, sodium salts of laurocholic, glycolic and desoxycholic acids and mixtures thereof.

Suitable terpenes include D-limonene, α-pinene, β-enrene, α-terpineol, terpinen-4-ol, carvol, carvone, pulegone, piperitone, menthone, menthol, geraniol, cyclohexene oxide, limonene oxide, α-pinene oxide, cyclopentene oxide, 1,8-cineole, ylang oil, anise oil, chenopodium oil, eucalyptus oil and mixtures thereof. Suitable alkanones include N-heptane, N-octane, N-nonane, N-decane, N-undecane, N-dodecane, N-tridecane, N-tetradecane, N-hexadecane and mixtures thereof. Suitable organic acids include citric acid, succinic acid, salicylic acid, salicylates (including the methyl, ethyl and propyl glycol derivatives), tartaric acid and mixtures thereof.

In a preferred embodiment, the penetration enhancer is an alkyl-2-(N-substituted amino)-alkanoate, an (N-substituted amino)-alkanol alkanoate, or a mixture of these. For convenient reference, alkyl-2-(N-substituted amino)-alkanoates and (N-substituted amino)-alkanol alkanoates can be grouped together under the label alkyl (N-substituted amino) esters.

Alkyl-2-(N-substituted amino)-alkanoates suitable for the present invention can be represented as follows:

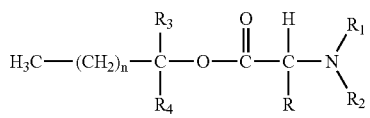

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

Preferred are alkyl (N,N-disubstituted amino)-alkanoates such as $C_4$ to $C_{18}$ alkyl (N,N-disubstituted amino)-acetates and $C_4$ to $C_{18}$ alkyl (N,N-disubstituted amino)-propionates and pharmaceutically acceptable salts and derivatives thereof. Exemplary specific alkyl-2-(N,N-disubstituted amino)-alkanoates include dodecyl 2-(N,N dimethylamino)-propionate (DDAIP);

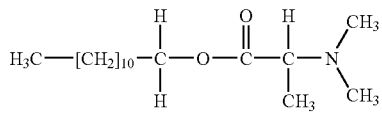

and dodecyl 2-(N,N-dimethylamino)-acetate (DDAA);

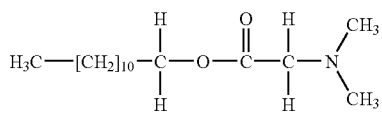

Alkyl-2-(N-substituted amino)-alkanoates are known. For example, dodecyl 2-(N,N-dimethylamino)-propionate (DDAIP) is available from Steroids, Ltd. (Chicago, Ill.). In addition, alkyl-2-(N,N-disubstituted amino)-alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

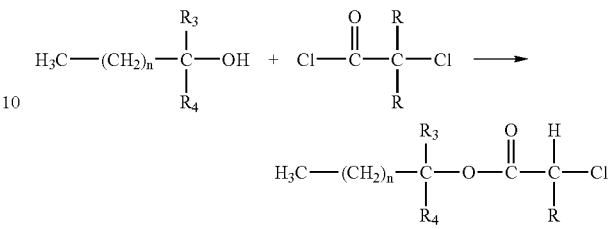

wherein R, $R_3$, $R_4$ and n are defined as above. The reaction temperature may be selected from about 10 degrees Celsius to about 200 degrees Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

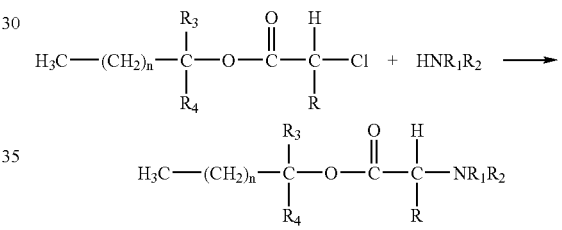

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable (N-substituted amino)-alkanol alkanoates can be represented by the formula:

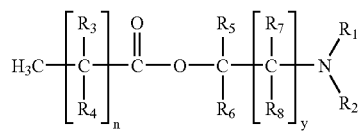

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are members of the group consisting of hydrogen, $C_1$ to $C_8$ alkyl, and $C_1$ to $C_8$ aryl; and $R_8$ is a member of the group consisting of hydrogen, hydroxyl, $C_1$ to $C_8$ alkyl, and $C_1$ to $C_8$ aryl. The preparation of suitable (N-substituted amino)-alkanol alkanoates and their advantages over previously known penetration enhancers are disclosed in published international patent application WO 95/09590.

Preferred are (N-substituted amino)-alkanol alkanoates such as $C_5$ to $C_{18}$ carboxylic acid esters and pharmaceutically acceptable salts thereof. Exemplary specific (N,N-disubstituted amino)-alkanol alkanoates include 1-(N,N-dimethylamino)-2-propanol dodecanoate (DAIPD);

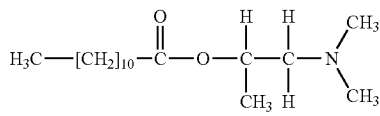

1-(N,N-dimethylamino)-2-propanol myristate (DAIPM);

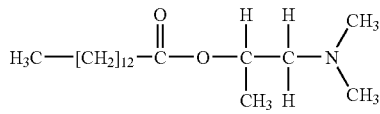

1-(N,N-dimethylamino)-2-propanol oleate (DAIPO);

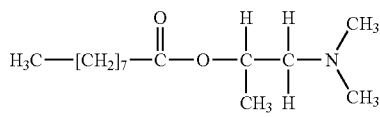

The (N,N-disubstituted amino)-alkanol alkanoates are readily prepared by reacting the corresponding aminoalkinol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethyl-amino)-2-propanol dodecanoate (DAIPD). Among the suitable penetration enhancers for the present invention DDAIP is generally preferred.

The penetration enhancer is present in an amount sufficient to enhance the penetration of the prostaglandin $E_1$. The specific amount varies necessarily according to the desired release rate and the specific form of prostaglandin $E_1$ used. Generally, this amount ranges from about 0.5 percent to about 10 percent, based on the total weight of the composition. In one embodiment, where the vasoactive prostaglandin is prostaglandin $E_1$, the penetration enhancer is DDAIP in the amount of about 0.01 to about 5 weight percent of the composition.

Additionally, other known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylaza-cycloheptane-2-one (Azone™, a registered trademark of Nelson Research), N,N-dimethylformamide, N-methyl-2-pyrrolidone, calcium thioglycolate, oxazolidinone, dioxolane derivatives, laurocapram derivatives, and macrocyclic enhancers such as macrocyclic ketones.

Natural and modified polysaccharide gums are also an important ingredient of the composition. Suitable representative gums are those in the natural and modified galactomannan gum category. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-manopyranosyl units, linked (1→6) with the main chain, are present as side branches. Galactomannan gums include guar gum, which is the pulverized endosperm of the seed of either of two leguminous plants (*Cyamposis tetragonalobus* and *psoraloids*) and locust bean gum, which is found in the endosperm of the seeds of the carobtree (*ceratonia siliqua*). Suitable modified polysaccharide gums include ethers of natural or substituted polysaccharide gums, such as carboxymethyl ethers, ethylene glycol ethers and propylene glycol ethers. An exemplary substituted polysaccharide gum is methylcellulose.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums: Polysaccharides & Their Derivatives*, Whistler R. L. and BeMiller J. N. (eds.), 3rd Ed. Academic Press (1992) and Davidson R. L., *Handbook of Water-Soluble Gums & Resins*, McGraw-Hill, Inc., N.Y. (1980). Most gums are commercially available in various forms, commonly a powder, and ready for use in foods and topical compositions. For example, locust bean gum in powdered form is available from Tic Gums Inc. (Belcam, Md.).

When present, the polysaccharide gums are present in the range from about 0.1 percent to about 5 percent, based on the total weight of the composition, with the preferred range being from 0.5 percent to 3 percent. In one preferred embodiment, 2.5 percent by weight of a polysaccharide gum is present. Illustrative compositions are given in the examples, below.

An optional alternative to the polysaccharide gum is a polyacrylic acid polymer. A common variety of polyacrylic acid polymer is known generically as "carbomer." Carbomer is polyacrylic acid polymers lightly cross-linked with polyalkenyl polyether. It is commercially available from the B. F. Goodrich Company (Akron, Ohio) under the designation "CARBOPOL™." A particularly preferred variety of carbomer is that designated as "CARBOPOL 940."

Other polyacrylic acid polymers suitable for use are those commercially available under the designations "Pemulen™" (B. F. Goodrich Company) and "POLYCARBOPHIL™" (A. H. Robbins, Richmond, Va.). The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers are present, they represent about 0.5 percent to about 5 percent of the composition, based on its total weight.

Semi-solid compositions and penetration enhancers suitable for the practice of the present invention are described in detail in U.S. Pat. Nos. 6,046,244, 6,118,020 and 6,323,241, the teachings of which are incorporated herein by reference.

The semi-solid composition has a suitably chosen viscosity such that the composition is naturally retained at the site of administration. The semi-solid composition can exhibit Newtonian or non-Newtonian rheological characteristics. In some preferred embodiments, the semi-solid composition of the present invention exhibits non-Newtonian rheological characteristics, i.e. in which the apparent viscosity is dependent on the shear rate applied to the composition. Preferably the composition has "shear-thinning" rheological properties. As used herein, "shear-thinning" refers to a reduction in apparent viscosity (the ratio of shear stress to the shear rate) with increasing shear rate, whether the reduction in apparent viscosity is time independent (pseudoplastic), time dependent (thixotropic) or associated with a yield stress, defined as a stress that must be exceeded before flow starts, (Bingham plastics and generalized Bingham plastics). See, generally, Harris, J., & Wilkinson, W. L., "Non-Newtonian Fluid," pp. 856-858 in Parker, S. P., ed., McGraw-Hill Encyclopedia of Physics, Second Edition, McGraw-Hill, New York, 1993. A suitable viscosity range of the composition is from about 5,000 centipoise (cps) to about 20,000 cps, preferably from about 7,000 cps to about 13,000 cps.

Another important component is a lipophilic component. As used herein "lipophilic component" refers to an agent that is both lipophilic and hydrophilic. One of ordinary skill in the pharmaceutical arts will understand that the lipophilic nature, or "lipophilicity" of a given compound is routinely quantified for comparison to other compounds by using the partition coefficient. The partition coefficient is defined by the International Union of Pure and Applied Chemistry (IUPAC) as the ratio of the distribution of a substance between two phases when the heterogeneous system (of two phases) is in equilibrium; the ratio of concentrations (or, strictly speaking, activities) of the same molecular species in the two phases is constant at constant temperature.

The $C_1$ to $C_8$ aliphatic alcohols, the $C_2$ to $C_{30}$ aliphatic esters, and their mixtures can serve as lipophilic component. Illustrative suitable alcohols are ethanol, n-propanol and isopropanol, while suitable esters are ethyl acetate, butyl acetate, ethyl laurate, methyl propionate, isopropyl myristate and isopropyl palmitate. As used herein, the term "aliphatic alcohol" includes polyols such as glycerol, propylene glycol and polyethylene glycols. In one embodiment, a mixture of alcohol and ester is preferred, and in particular, a mixture of ethanol and ethyl laurate is preferred. In another embodiment, about 0.1 to about 10 percent by weight isopropyl myristate, preferably about 3 percent by weight isopropyl myristate is substituted for ethyl laurate. In some embodiments, the lipophilic component includes at least one liquid polyol. In preferred embodiments, the liquid polyol is a polyethylene glycol selected from the group consisting of polyethylene glycol 200, polyethylene glycol 400 and polyethylene glycol 600. When polyethylene glycol is used, polyethylene glycol is present in the amount of about 1 weight percent to about 25 weight percent, based on the total weight of the composition. A preferred polyethylene glycol is polyethylene glycol 400 (PEG 400). When present, polyethylene glycol 400 is about 1 weight percent to about 25 weight percent, preferably about 3 weight percent to about 20 weight percent, based on the total weight of the composition.

In one embodiment, the $C_2$ to $C_{30}$ aliphatic esters, and their mixtures comprising the lipophilic component include $C_8$ to $C_{30}$ aliphatic esters of glycerol selected from the group consisting of monoglycerides, diglycerides, triglycerides, and mixtures thereof. Suitable aliphatic esters include glyceryl esters of saturated fatty acids, unsaturated fatty acids and mixtures thereof. Suitable saturated fatty acids include caproic acid, caprylic acid, capric acid, lauric acid, myristic acid, palmitic acid, stearic acid, arachidic acid, behenic acid and lignoceric acid. In a preferred embodiment, about 0.1 to about 5 percent, preferably about 1 weight percent lauric acid is present. Suitable unsaturated fatty acids include oleic acid, linoleic acid and linolenic acid. Suitable glyceryl esters include glyceryl monooleate, triolein, trimyristin and tristearin, preferably trimyristin.

The concentration of lipophilic component required necessarily varies according to other factors such as the desired semi-solid consistency and the desired skin penetration promoting effects. Suitably the concentration of lipophilic component is in the range of 0.5 percent to 40 percent by weight based on the total weight of the composition. The preferred topical composition contains lipophilic component in the range of 7 percent to 40 percent by weight based on the total weight of the composition.

Where a mixture of aliphatic alcohol and aliphatic ester are employed, the suitable amount of alcohol is in the range of 0.5 percent to 10 percent. In one preferred embodiment, the amount of alcohol is in the range of 5 percent to 15 percent, while that of aliphatic ester is in the range from 2 percent to 15 percent (again based on the total weight of the composition).

In another preferred embodiment, the amount of alcohol is in the range of 0.5 percent to 10 percent, while that of aliphatic ester is in the range from 0 percent to 10 percent (again based on the total weight of the composition).

The concentration of lipophilic component required necessarily varies according to other factors such as the desired semi-solid consistency and the desired skin penetration promoting effects. The preferred topical composition contains lipophilic component in the range of 7 percent to 40 percent by weight based on the total weight of the composition. Where a lipophilic component that is a mixture of aliphatic alcohol and aliphatic ester is used, the preferred amount of alcohol is in the range of 5 percent to 15 percent, while that of aliphatic ester is in the range from 2 percent to 15 percent (again based on the total weight of the composition).

An optional, but preferred, component is an emulsifier. Although not a critical factor, a suitable emulsifier generally will exhibit a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred, and a ratio of 1 to 4 is most preferred to generate the desired semi-solid consistency and separation resistance.

Other emulsifiers are also suitable including polyoxyethylene sorbitan esters, long chain alcohols, preferably cetostearyl alcohol, and fatty acid glycerides. Suitable polyoxyethylene sorbitan esters include the monolaurate (Tween 20, Span 20) the monopalmitate (Tween 40), the monostearate (Tween 60), and the monooleate (Tween 80) and mixtures thereof. Preferred fatty acid glycerides include glyceryl monooleate, triolein, trimyristin and tristearin.

The composition includes an acid buffer system. Acid buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While there are countless suitable buffers, potassium phosphate monohydrate has proven effective for compositions of the present invention.

The final pH value of the pharmaceutical composition may vary within the physiologically compatible range. Necessarily, the final pH value is not irritating to human skin. Without violating this constraint, the pH may be selected to improve prostaglandin $E_1$ stability and to adjust consistency when required. In one embodiment, the preferred pH value is about 3 to about 7.4, more preferably about 3.0 to about 6.5, most preferably from about 3.5 to about 6.0.

The remaining component of the composition is water, which is necessarily purified. The composition contains water in the range of about 50 to about 90 percent, based on the total weight of the composition. The specific amount of water present is not critical, however, being adjustable to obtain the desired consistency and/or concentration of the other components.

Prostaglandin $E_1$ stabilizers, coloring agents, Theological agents, and preservatives can be added to the extent that they do not overly limit prostaglandin $E_1$ skin penetration or prevent the desired semi-solid consistency.

Contemplated dosage forms of the semi-solid pharmaceutical composition are creams, gels, ointments, colloidal suspensions and the like, also including but not limited to compositions suitable for use with transdermal patches and like devices.

The ingredients listed above may be combined in any order and manner that produces a stable composition comprising a prostaglandin $E_1$ evenly dispersed throughout a semi-solid formulation. One available approach to preparing such compositions involves evenly dispersing the polysaccharide gum (or polyacrylic acid polymer) in a premixed water/buffer solution and then thoroughly homogenizing (i.e. mixing) the resulting mixture, which can be labeled "Part A." When present, the emulsifier is added to the water/buffer solution before dispersing the polysaccharide gum. Any suitable method of adjusting the pH value of Part A to the desired level may be used, for example, by adding concentrated phosphoric acid or sodium hydroxide.

Separately, the prostaglandin $E_1$ is dissolved with agitation in the lipophilic component, which itself may be a mixture of alcohols, esters, or alcohol with ester. Next, the penetration enhancer is added. Alternatively, when the lipophilic component includes both an alcohol and an ester, the prostaglandin $E_1$ can be dissolved in the alcohol before adding the penetration enhancer followed by the ester. In either case, the resulting mixture can be labeled "Part B." The final step involves slow addition (e.g. dropwise) of Part B into Part A under constant mixing.

The resulting topical composition, when compared to exhibits the advantageous properties described above, including improved prostaglandin $E_1$ permeation and bioavailability without drug overloading, reduced skin damage and related inflammation, and increased flexibility in design of dosage forms. These compositions can be used for prolonged treatment of peripheral vascular disease, male impotency and other disorders treated by prostaglandin $E_1$, while avoiding the low bioavailability and rapid chemical decomposition associated with other delivery methods. Application of prostaglandin $E_1$ in a topical composition to the skin of a subject allows a predetermined amount of prostaglandin $E_1$ to be administered continuously to the subject and avoids undesirable effects present with a single or multiple administrations of larger dosages by injection. By maintaining a sustained dosage rate, the prostaglandin $E_1$ level in the subject's target tissue can be better maintained within the optimal therapeutic range.

In one embodiment, a composition comprises about 0.01 percent to about 5 percent modified polysaccharide gum; about 0.001 percent to about 1 percent of a prostaglandin selected from the group consisting of $PGE_1$, pharmaceutically acceptable salts thereof, lower alkyl esters thereof and mixtures thereof; about 0.5 percent to about 10 percent DDAIP or salts thereof; about 0.5 percent to about 10 percent of a lower alcohol selected from the group consisting of ethanol, propanol, isopropanol and mixtures thereof; about 0.5 percent to about 10 percent on an ester selected from the group consisting of ethyl laurate, isopropyl myristate, isopropyl laurate and mixtures thereof; based on the weight of the composition, and an acid buffer. Preferably the composition also comprises up to about 2 percent sucrose stearate.

Optionally the composition also comprises up to about 5 percent emulsifier. Preferably, the composition also comprises up to about 2 percent emulsifier. Suitable emulsifiers include polysorbates such as Tweens, glyceryl monooleate, triolein, trimyristin and tristearin. A preferred emulsifier is trimyristin.

The practice of the present invention is demonstrated in the following examples. These examples are meant to illustrate the invention rather than to limit its scope. Variations in the treating compositions which do not adversely affect the effectiveness of prostaglandin $E_1$ will be evident to one skilled in the art, and are within the scope of this invention. For example, additional ingredients such as coloring agents, antimicrobial preservatives, emulsifiers, perfumes, prostaglandin $E_1$ stabilizers, and the like may be included in the compositions as long as the resulting composition retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). Suitable perfumes and fragrances are known in the art; a suitable fragrance is up to about 5 percent myrtenol, preferably about 2 percent myrtenol, based on the total weight of the composition. The compositions of the present invention can also include a small amount, about 0.01 to about 4% by weight, of a topical anesthetic, if desired. Typical topical anesthetics include lidocaine, dyclonine, dibucaine, pharmaceutically acceptable salts and mixtures thereof. In one preferred embodiment, the topical anesthetic is about 0.5 percent dyclonine, based on the weight of the composition.

The pharmaceutical preparation is preferably in unit dosage form. In such form the preparation is subdivided into unit doses containing appropriate quantities of the active component. The unit dosage form is a packaged preparation, where the package containing the discrete quantities of the pharmaceutical preparation is, e.g. a rigid plastic dispenser or flexible packet.

Another aspect of the invention is an article of manufacture that comprises a composition for treating erectile dysfunction as described above in a suitable container, preferably in a container such as the dispenser disclosed in U.S. Pat. No. 6,224,573, in combination with labeling instructions. Alternatively, the container can be a tube with a suitable orifice size, such as an extended tip tube, pouch, packet, or squeeze bottle and made of any suitable material, for example rigid plastic or flexible plastic.

The labeling instructions can come in the form of a pamphlet, a label applied to or associated with the packaging of the article of manufacture.

Unless otherwise indicated, each composition is prepared by conventionally admixing the respective indicated components together.

Example 1

Exemplary Compositions

Exemplary Composition A was prepared as follows. Part A was formed by dissolving 0.4 parts prostaglandin $E_1$ (Alprostadil USP) in 5 parts ethyl alcohol. Next, 5 parts dodecyl 2-(N,N-dimethylamino)-propionate were mixed into the alcohol-prostaglandin $E_1$ solution, followed by 5 parts ethyl laurate.

Part B was prepared starting from a pH 5.5 water/buffer solution. The water/buffer solution was prepared by adding sufficient potassium phosphate monohydride to purified water to create a 0.1 M solution. The pH of the water/buffer solution was adjusted to 5.5 with a strong base solution (1 N sodium hydroxide) and a strong acid (1 N phosphoric acid). The buffer solution represented about 80 parts of the total composition. All parts specified herein are parts by weight.

To the buffer solution was added 0.5 parts ethyl laurate. Next, the locust bean gum (in powder form) was dispersed in the buffer solution and homogenized using a homogenizer. Table 1, below, contains a list of ingredients.

The resulting composition was a spreadable, semi-solid suitable for application to the skin without the need for supporting devices such as patches and adhesive strips. The composition was both homogenous in appearance and resistant to separation.

TABLE 1

Topical Prostaglandin $E_1$ Compositions

| Ingredient (wt %) | A | B | C | D | E | F | G | H | I |
|---|---|---|---|---|---|---|---|---|---|
| prehydrated locust bean gum | 3 | 3 | 3 | 3 | 3 | 3 | 3 | — | — |
| prehydrated modified guar gum | — | — | — | — | — | — | — | 3 | — |
| Xanthan gum | — | — | — | — | — | — | — | — | 2 |
| water/buffer (pH 5.5) | 81 | 81 | 81 | 81 | 81 | 81 | 81 | 81 | 82.7 |
| sucrose stearate | 0.5 | 0.5 | 0.5 | 0.5 | 0.5 | 0.5 | 0.5 | — | — |
| prostaglandin $E_1$ | 0.1 | 0.2 | 0.3 | 0.4 | 0.4 | 0.5 | 0.4 | 0.3 | 0.4 |
| DDAIP | 5 | 5 | 5 | 5 | 5 | 5 | 5 | 2.5 | 1.8 |
| ethanol | 5 | 5 | 5 | 5 | 5 | 5 | 10 | 5 | 5 |
| ethyl laurate | 5 | 5 | 5 | 5 | 5 | 5 | — | 3 | — |
| Isopropyl myristate | — | — | — | — | — | — | — | — | 3 |
| triethanolamine | — | — | — | — | — | — | — | — | 0.5 |
| lauric acid | — | — | — | — | — | — | — | — | 1 |

Additional exemplary compositions B-I are prepared in the same manner using the components listed in Table 1. As noted above, in other embodiments, such as Composition H, the composition may include a modified polysaccharide gum, suitably a modified galactomannan gum, such as a guar gum. Alternatively, a polyacrylic acid polymer may be used instead of the polysaccharide gum.

Example 2

Pharmacodynamic Study of a Topical $PGE_1$ Composition as an Antagonist for Vasospasm The spasmolysis (reversal of vasospasm) and vasodilation effects of a topical $PGE_1$ composition (Composition H of Example 1 modified as appropriate to contain the indicated amount of $PGE_1$) on vasospasm induced by adrenalin hydrochloride were studied in vivo by monitoring vascular diameter changes in rabbit ears.

TABLE 2

Drugs Used

| Drug Name | Size | Function | Batch No. | Supplier |
|---|---|---|---|---|
| Sumianxin | 1.5 ml/Ampule | General Anesthesia | 20020425 | Veterinary Research Institute of Changchun Agricultural-Pastoral University |
| Adrenaline HCl | 1 mg/1 ml | Vasospasm Induction | 20010625 | Tianjing People's Pharmaceuticals |
| Blank Sterile Cream | 0.0% $PGE_1$ | Blank Control | 020401 | NexMed Pharmaceuticals (Zhongshan), Ltd. |
| $PGE_1$ Sterile Cream | 0.4% $PGE_1$ w/o penetration enhancers | Positive Control | 020401 | |
| | 0.1% $PGE_1$ | Test Composition | 020401 | |
| | 0.2% $PGE_1$ | | 020401 | |
| | 0.4% $PGE_1$ | | 020401 | |
| | 0.8% $PGE_1$ | | 020401 | |

Note:
Positive control was 0.4% $PGE_1$ sterile cream without DDAIP penetration enhancer; all other $PGE_1$ cream preparations contained 2.5 wt% DDAIP penetration enhancer. Sumianxin is a mixture of baodingning (5% dimethyl aniline thiazole hydrochloride with 10% EDTA) and haloperidol.

Note: Positive control was 0.4% $PGE_1$ sterile cream without DDAIP penetration enhancer; all other $PGE_1$ cream preparations contained 2.5 wt % DDAIP penetration enhancer. Sumianxin is a mixture of baodingning (5% dimethyl aniline thiazole hydrochloride was 10% EDTA) and haloperidol.

New Zealand Rabbits, weight 2-3 kg, no gender preference, used in the study were provided by the Breed Branch of Beijing Yuancheng Miaomu Company, Ltd., license No. SCK2002-004. General anesthesia was induced by intramuscular injection of SUMIANXIN (0.3 ml/kg). A total of 60 rabbits were randomly assigned into 6 groups with 10 rabbits per group. Testing was preformed at a constant room temperature of 20 degrees Celsius. Blood vessels were imaged and recorded using a Sony DSC-S75 Digital Camera. Vessel diameters were measured using Adobe Photoshop 6.0 Software.

After shaving and preparation of the rabbit ears, 0.05 ml of adrenaline hydrochloride (1 mg/ml) was injected into the tissue surrounding the central artery 1 cm above the base of the ear. The vasospasm was typically observed about five minutes after the adrenalin injection. A single administration of 80 mg topical composition with various $PGE_1$ concentrations was applied onto the skin area, 0.5-2 cm above the ear base, 10 minutes after the appearance of the typical vasospasm in the central ear artery. Administration of $PGE_1$ at a concentration of 0.1, 0.2, 0.4 and 0.8 weight percent provided respective doses of 80, 160, 320 and 640 micrograms (μg) of $PGE_1$. Digital photographs were taken of the normal condition of the blood vessels after anesthesia, at 10 minutes after vasospasm was induced, and at 10, 15, 30, 60, 90 and 120 minutes after the administration of the various $PGE_1$ topical compositions.

The digital images were uploaded into a computer and analyzed using Adobe Photoshop 6.0 software. The diameter of the central artery at a point 1.5 cm above the base of the ear was measured with an accuracy of 0.1 mm. The data are reported in Table 3, below, as mean diameter±standard deviation (SD); t-test was used for statistical analysis.

TABLE 3

Vessel Diameter Before And After Administration of Cream

| Group<br>N | 80 μg<br>10 | 160 μg<br>10 | 320 μg<br>10 | 640 μg<br>10 | Positive<br>Control<br>10 | Blank<br>Control<br>10 |
|---|---|---|---|---|---|---|
| Normal Condition after Anesthesia | 2.9 ± 0.13 | 2.5 ± 0.13 | 2.7 ± 0.12 | 2.8 ± 0.15 | 2.8 ± 0.17 | 2.8 ± 0.20 |
| 10 minutes after Vasospasm | 0.7 ± 0.14 | 0.5 ± 0.12 | 0.6 ± 0.11 | 0.4 ± 0.08 | 0.4 ± 0.12 | 0.6 ± 0.12 |
| 10 minutes after Application | 1.1 ± 0.18 | 1.6 ± 0.12 | 2.5 ± 0.16 | 2.6 ± 0.09 | 1.4 ± 0.13 | 1.2 ± 0.16 |
| 15 minutes after Application | 2.0 ± 0.16 | 2.3 ± 0.15 | 2.8 ± 0.14 | 2.8 ± 0.16 | 1.4 ± 0.18 | 1.4 ± 0.15 |
| 30 minutes after Application | 2.1 ± 0.14 | 2.5 ± 0.16 | 2.8 ± 0.17 | 2.8 ± 0.13 | 1.4 ± 0.16 | 1.4 ± 0.22 |
| 60 minutes after Application | 1.1 ± 0.18 | 2.1 ± 0.18 | 3.2 ± 0.18 | 3.2 ± 0.12 | 1.4 ± 0.16 | 1.5 ± 0.17 |
| 90 minutes after Application | 1.4 ± 0.16 | 2.1 ± 0.16 | 2.8 ± 0.19 | 3.2 ± 0.13 | 1.4 ± 0.14 | 1.5 ± 0.16 |
| 120 minutes after Application | 1.7 ± 0.22 | 2.1 ± 0.17 | 2.8 ± 0.20 | 2.8 ± 0.19 | 1.8 ± 0.24 | 2.0 ± 0.18 |

Figure 1B:

FIGS. 1A-1B shows images of the transilluminated shaved dorsal surfaces of the right (FIG. 1A) and left ears (FIG. 1B) of a rabbit. The two arrows in each Fig. indicate the vasospasm that was observed 5 minutes after injections of 2 ml of a 0.1% adrenaline solution into the tissue next to the central arteries and veins near the base of both ears.

Figure 2A:
FIG. 2 shows images of the transilluminated shaved dorsal surfaces of the right (FIG. 2A) and left ears (FIG. 2B) of the rabbit of FIG. 1 about five minutes after topical application of 125 mg of a topical composition comprising 0.4 weight percent (wt %) $PGE_1$ onto the skin adjacent to the central artery and vein near the bottom of the right ear (FIG. 2A). At 15 minutes post application, all blood vessels on the right ear were dilated, including the site of the vasospasm (between the two arrows). All blood vessels were dilated normally and showed good circulation thirty-five minutes after the application. In comparison, the blood vessels of the left ear that was treated with the blank control remained in vasospasm (arrows, FIG. 2B).
Figure 2B:
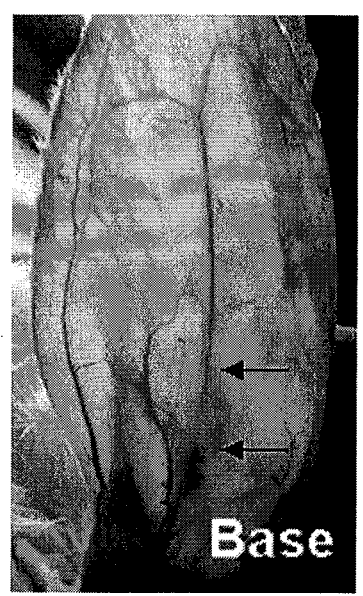

FIGS. 2A-2B show images of the transilluminated shaved dorsal surfaces of the right (FIG. 2A) and left ears (FIG. 2B) of the rabbit of FIG. 1 about five minutes after topical application of 125 mg 0.4% topical $PGE_1$ composition onto the skin next to the central artery and vein near the bottom of the right ear (FIG. 2A). At 15 minutes post application, all blood vessels on the right ear were dilated, including the site of the vasospasm (between the two arrows. At 35 minutes after the application, all blood vessels were dilated normally and showed good circulation. In comparison, the blood vessels of the left ear that was treated with the blank control remained in vasospasm (arrows, FIG. 2B).

Figure 3:
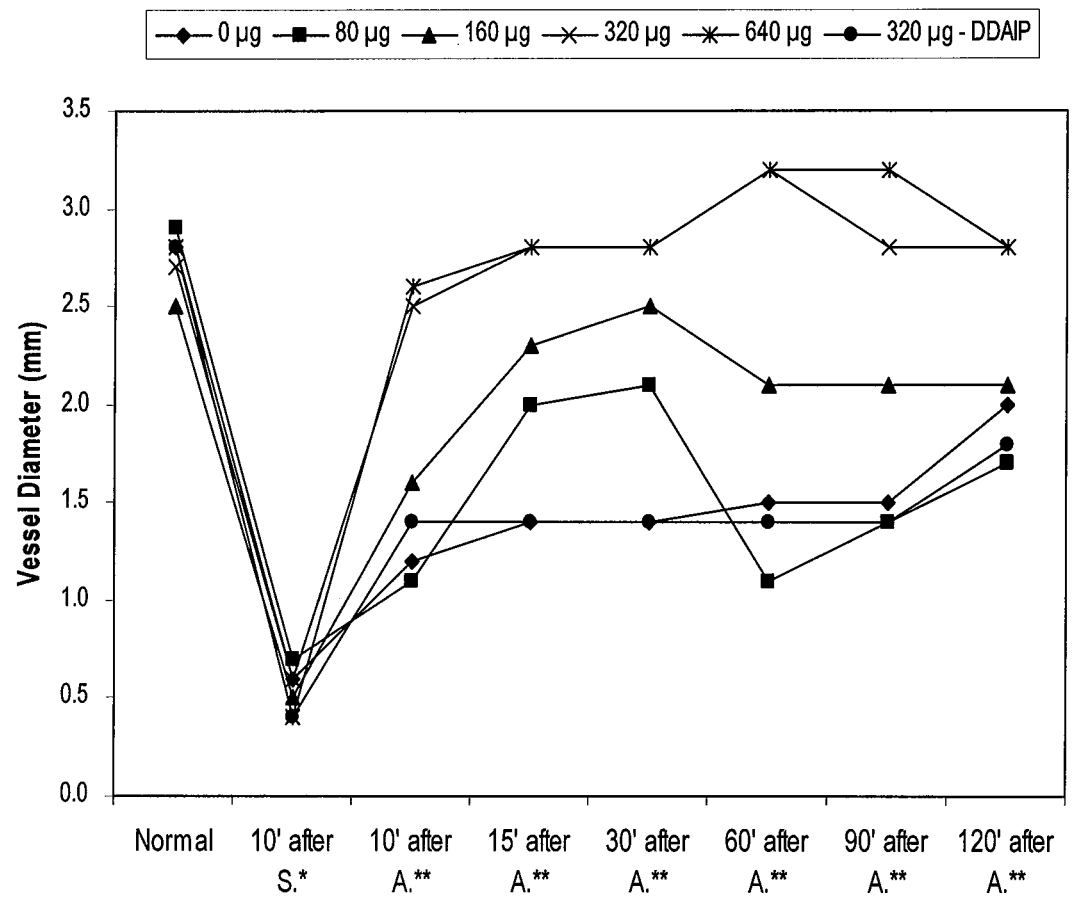
FIG. 3 is a graphical representation of the averaged results of a study of vasospasm in rabbit ears that is illustrated by FIG. 1 and FIG. 2. As noted above, a single administration of 80 mg topical composition with various $PGE_1$ concentrations was applied onto the skin area, 0.5-2 cm above the ear base, 10 minutes after the typical time a vasospasm appeared in the central ear artery. Administration of the topical composition comprising 0.1, 0.2, 0.4 or 0.8 weight percent $PGE_1$ provided respective doses of 80 (filled circles), 160 (filled triangles), 320 ("X") and 640 ("*") micrograms (μg) of $PGE_1$ as well as cream without $PGE_1$ (0 μg $PGE_1$, filled diamonds) and positive control (0.4% $PGE_1$ topical composition without penetration enhancer, filled circles).

The averaged data are reported in Table 3, above, as mean diameter±standard deviation (SD), N=10, and shown graphically in FIG. 3. FIG. 3 is a graphical representation of the averaged results of a study of vasospasm in rabbit ears that is illustrated by FIG. 1 and FIG. 2. As noted above, a single administration of 80 mg topical composition with various $PGE_1$ concentrations was applied onto the skin area, 0.5-2 cm above the ear base, 10 minutes after the typical time a vasospasm appeared in the central ear artery. Administration of the topical composition comprising 0.1, 0.2, 0.4 or 0.8 weight percent $PGE_1$ provided respective doses of 80 (filled circles), 160 (filled triangles), 320 ("X") and 640 ("*") micrograms (μg) of $PGE_1$ as well as cream without $PGE_1$ (0 μg $PGE_1$, filled diamonds) and positive control (0.4% $PGE_1$ topical composition without penetration enhancer, filled circles). Digital photographs were taken of the normal condition of the blood vessels after anesthesia, at 10 minutes after vasospasm was induced, and at 10, 15, 30, 60, 90 and 120 minutes after the administration of the various $PGE_1$ compositions. Data are presented as mean vessel diameter±standard deviation. S* refers to the time of the vasospasm; A** refers to the time of the administration of topical composition.

TABLE 4

The Average Time (minutes) Required To Return
To The Initial Vessel Diameter.
(N = 10 for each group)

| 0 μg<br>(Blank<br>Control) | 320 μg<br>without<br>DDAIP<br>(Positive<br>Control<br>in This<br>Study) | 80 μg | 160 μg | 320 μg | 640 μg |
|---|---|---|---|---|---|
| 120 | 120 | 120 | 30 ± 16.37 | 15 ± 18.18 | 10 ± 11.11 |

The average time required to return to the initial vessel diameter is provided in Table 4, above. The treatment with the blank control composition ("0 μg $PGE_1$"), 0.4% $PGE_1$ topical composition without DDAIP penetration enhancer and a topical composition comprising 80 μg $PGE_1$ did not produce recovery of vessel diameter within the 120 minute duration of the test. Administration of topical compositions having higher amounts of $PGE_1$ produced recovery of vessel diameter and showed a dose-dependent decrease in the time required for recovery. In this study, there was a more than six-fold difference between compositions with and without DDAIP at the 320 mg dose of $PGE_1$, a supra threshold effective dose.

TABLE 5

The Duration (minutes) The Initial Vessel Diameter
Was Greater Than The Diameter Before Vasospasm.
(N = 10 for each group)

| 0 μg<br>0 wt %<br>$PGE_1$<br>(Blank<br>Control) | 320 μg<br>0.4 wt %<br>$PGE_1$<br>without<br>DDAIP<br>(Positive<br>Control in<br>This Study) | 80 μg<br>0.1 wt %<br>$PGE_1$ | 160 μg<br>0.2 wt %<br>$PGE_1$ | 320 μg<br>0.4 wt %<br>$PGE_1$ | 640 μg<br>0.8 wt %<br>$PGE_1$ |
|---|---|---|---|---|---|
| 0 | 30 | 0 | 5 | 105 | 120 |

The average time required to return to the initial vessel diameter is provided in Table 5, above, showing additional vasodilation beyond the baseline. The treatment with the blank control composition, 0.4% $PGE_1$ topical composition without DDAIP penetration enhancer and a topical composition comprising 0.1 wt % $PGE_1$ did not produce any time within the 120 minute duration of the test when the vessel diameter was greater than the pre-vasospasm value. Administration of topical compositions having higher amounts of $PGE_1$ resulted in dose-dependent dilation of the vessels. "Positive" indicates the result obtained with the composition that contained 320 μg (0.4 wt %) $PGE_1$ but lacked DDAIP. Note that in this study there was more than a three-fold difference seen in the effects of compositions with and without DDAIP with the same effective doses, 320 μm, of $PGE_1$.

At Ten and Fifteen Minutes after Administration of the Drug:

Compared to blank control group, the changes in vessel diameter produced by 80 μg $PGE_1$ cream and the positive control composition were not significant ($P>0.05$), but the changes in vessel diameter produced by the rest of the other $PGE_1$ compositions were significant at the $P<0.01$ level. Significant differences ($P<0.01$) were observed between all treatments except between 320 μg and 640 μg $PGE_1$ treatments ($P>0.05$).

At 30 Minutes after Administration of the Drug:

Compared to blank control treatment, significant differences ($P<0.01$) in vascular diameter changes were observed for treatment with each of the $PGE_1$ concentrations except the positive control treatment ($P>0.05$). Among experimental treatments, significant differences ($P<0.01$) were observed between all treatments except between 320 μg and 640 μg $PGE_1$ treatments ($P>0.05$).

At 60 Minutes and at 90 Minutes after Administration of the Drug:

Compared to blank control treatment, significant differences ($P<0.01$) in the vascular diameter changes were observed for treatment with each of the $PGE_1$ concentrations except the 80 μg treatment and the positive control treatment ($P>0.05$). Among experimental treatments, significant differences ($P<0.01$) were observed between all treatments except between 320 μg and 640 μg $PGE_1$ treatments ($P>0.05$).

At 120 Minutes after Administration of the Drug:

Compared to blank control group, significant differences ($P<0.01$) of the vascular diameter changes were observed for treatment with each of the $PGE_1$ concentrations except the 80 μg, 160 μg $PGE_1$ and the positive control treatments ($P>0.05$). Among experimental groups, significant differences ($P<0.01$) were observed between all treatments except between 320 μg and 640 μg $PGE_1$ treatments ($P>0.05$).

The results showed that, compared to the blank control group, significant differences ($P<0.01$) were observed for 320 μg and 640 μg $PGE_1$ treatments at every time point, while no significant changes were found between these latter two groups ($P<0.05$). While a dose-dependent effect was observed in the range 0.2-0.8 weight percent $PGE_1$ for topical compositions having the DDAIP penetration enhancer, a topical composition having 0.4 weight percent $PGE_1$ but lacking DDAIP had effects comparable to those of the blank control that lacked $PGE_1$.

Example 3

Laser Doppler Study of Vascular Perfusion Volume Charges in Treatment of Vasospasm using a Topical $PGE_1$ Composition The spasmolysis (reversal of vasospasm) and vasodilation effects of a topical $PGE_1$ composition (Composition H of Example 1 modified as appropriate to contain the indicated amount of $PGE_1$) on vasospasm induced by adrenalin hydrochloride were studied by monitoring vascular perfusion volume changes of central arteries of rabbit ears. Rabbits were obtained and anesthetized and vasospasm induced as described in Example 2, above. A total of 60 rabbits were randomly assigned into 6 groups with 10 rabbits per group.

Vascular perfusion volume and skin temperature were measured using the PeriFlux 5000 laser Doppler blood flowmetry system (Perimed AB, Stockholm, Sweden). As in Example 2, above, a single administration of 80 mg topical composition with various $PGE_1$ concentrations was applied onto the skin area, 0.5-2 cm above the ear base, 10 minutes after the appearance of the typical vasospasm in the central ear artery. The laser probe was fixed at the area of central artery about 1.5 cm above the ear base. Measurements were made at time points of normal condition after anesthesia, 10 minutes after vasospasm, 10 minutes, 15 minutes, 30 minutes, 60 minutes, 90 minutes, and 120 minutes after administration of the drug.

TABLE 6

The vascular perfusion volume changes before and after the drug administration (ml/min)

| Group N | 80 μg 10 | 160 μg 10 | 320 μg 10 | 640 μg 10 | Positive Control 10 | Blank Control 10 |
|---|---|---|---|---|---|---|
| Normal Condition after Anesthesia | 124 ± 4.90 | 128 ± 4.45 | 127 ± 3.33 | 123 ± 3.06 | 127 ± 5.84 | 126 ± 4.69 |
| 10 minutes after Vasospasm | 14 ± 1.49 | 17 ± 1.70 | 15 ± 1.94 | 13 ± 2.16 | 15 ± 3.16 | 12 ± 2.00 |
| 10 minutes after Application | 19 ± 1.16 | 40 ± 2.40 | 126 ± 6.15 | 139 ± 10.84 | 25 ± 2.94 | 16 ± 2.06 |
| 15 minutes after Application | 20 ± 1.94 | 90 ± 3.02 | 145 ± 6.70 | 170 ± 4.67 | 24 ± 1.70 | 20 ± 2.98 |
| 30 minutes after Application | 97 ± 6.15 | 130 ± 5.94 | 152 ± 6.29 | 196 ± 5.87 | 25 ± 2.54 | 30 ± 4.88 |
| 60 minutes after Application | 56 ± 7.69 | 85 ± 4.59 | 197 ± 3.97 | 205 ± 2.79 | 29 ± 1.83 | 35 ± 5.03 |
| 90 minutes after Application | 63 ± 6.80 | 94 ± 4.11 | 152 ± 4.88 | 196 ± 5.44 | 50 ± 6.93 | 48 ± 5.93 |
| 120 minutes after Application | 95 ± 10.33 | 92 ± 3.68 | 146 ± 3.33 | 167 ± 7.10 | 62 ± 5.89 | 70 ± 7.33 |

Figure 4:
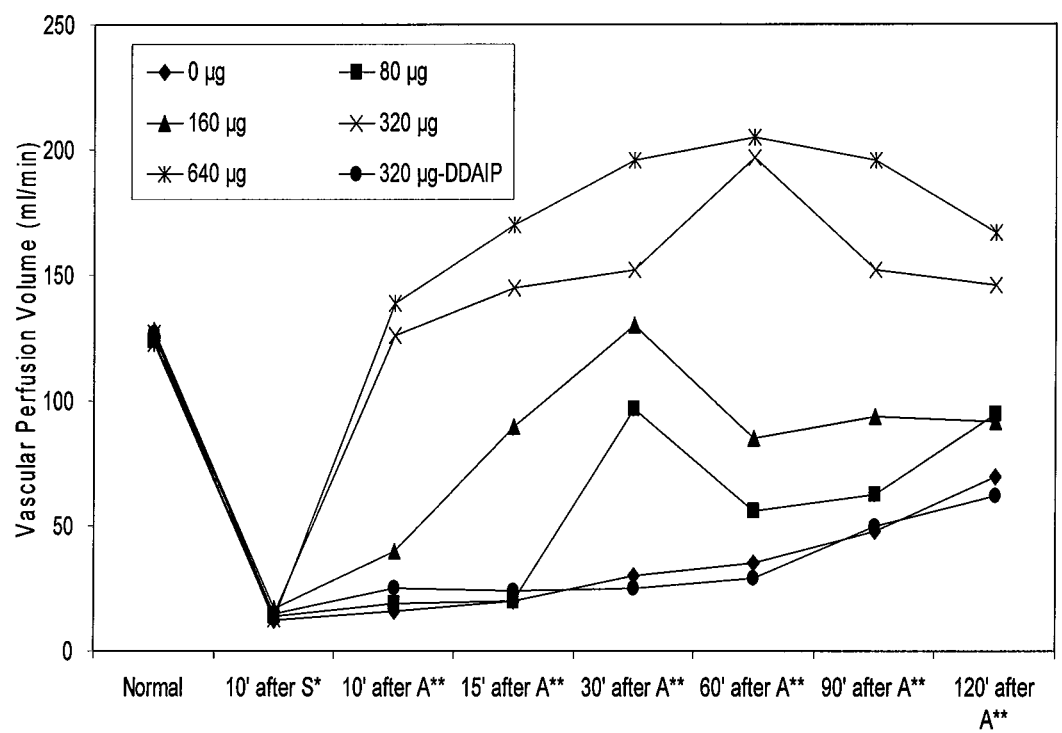
FIG. 4 is a graphical representation of the averaged results of a study of vascular perfusion volume in vasospasm in rabbit ears as measured by transcutaneous laser Doppler blood flowmetry. As noted above, a single administration of 80 mg topical composition with various $PGE_1$ concentrations was applied onto the skin area, 0.5-2 cm above the ear base, 10 minutes after the typical time a vasospasm appeared in the central ear artery. Administration of the topical composition comprising 0.1, 0.2, 0.4 or 0.8 weight percent $PGE_1$ provided respective doses of 80 (filled circles), 160 (filled triangles), 320 ("X") and 640 ("*") micrograms (μg) of $PGE_1$ as well as cream without $PGE_1$ (0 μg $PGE_1$, filled diamonds) and positive control (0.4% $PGE_1$ topical composition without penetration enhancer, filled circles). Measurements were taken of the normal condition of the blood vessels after anesthesia, at 10 minutes after vasospasm was induced, and at 10, 15, 30, 60, 90 and 120 minutes after the administration of the various $PGE_1$ compositions. Data are presented as mean±standard deviation. S* refers to the time of the vasospasm; A** refers to the time of the administration of topical composition.
Figure 5A:
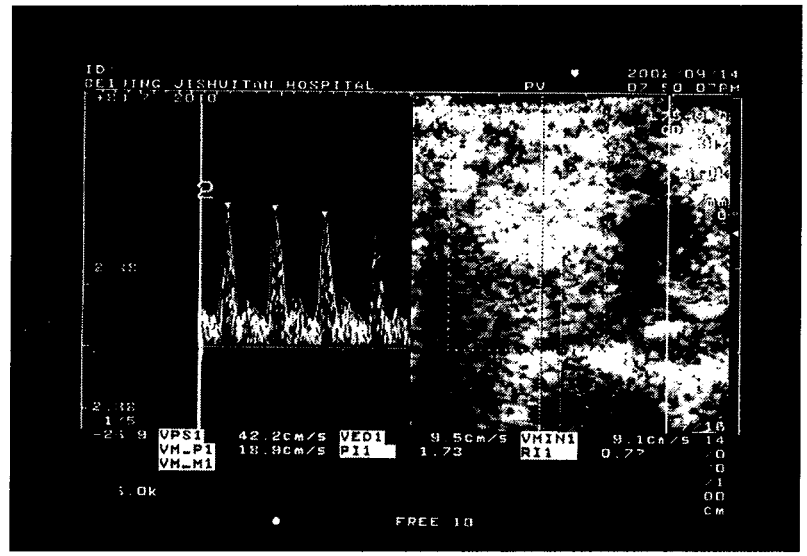
FIG. 5A and FIG. 5B show ultrasonograms of blood flow in the femoral artery of a rabbit.
Figure 5B:
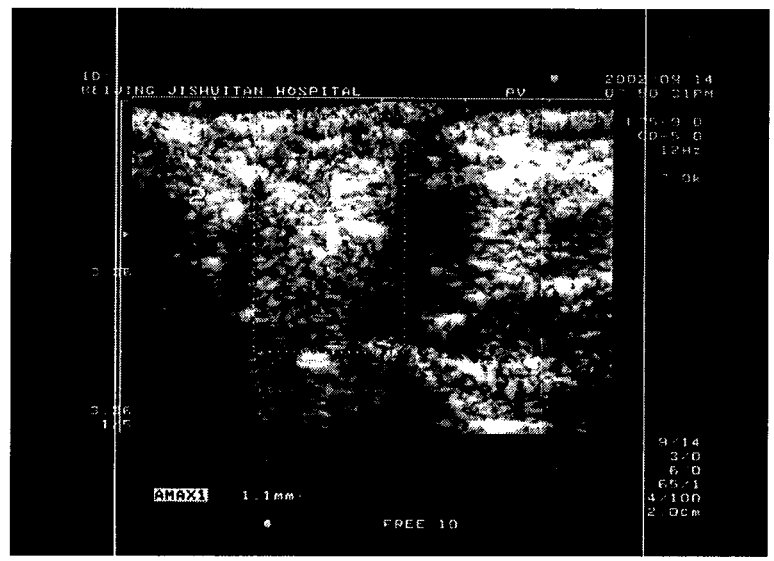

The averaged data are reported in Table 6, above, as mean vascular perfusion volume±standard deviation (SD), N=10, and shown graphically in FIG. 4. FIG. 4 is a graphical representation of the averaged results of a study of vascular perfusion volume in vasospasm in rabbit ears as measured by transcutaneous laser Doppler blood flowmetry. As noted above, a single administration of 80 mg topical composition with various $PGE_1$ concentrations was applied onto the skin area, 0.5-2 cm above the ear base, 10 minutes after the typical time a vasospasm appeared in the central ear artery. Administration of the topical composition comprising 0.1, 0.2, 0.4 or 0.8 weight percent $PGE_1$ provided respective doses of 80 (filled circles), 160 (filled triangles), 320 ("X") and 640 ("*") micrograms (μg) of $PGE_1$ as well as cream without $PGE_1$ (0 μg $PGE_1$, filled diamonds) and positive control (0.4% $PGE_1$ topical composition without penetration enhancer, filled circles). Measurements were taken of the normal condition of the blood vessels after anesthesia, at 10 minutes after vasospasm was induced, and at 10, 15, 30, 60, 90 and 120 minutes after the administration of the various $PGE_1$ compositions. Data are presented as mean±administration of topical composition. Positive control, 0 μg and 80 μg groups did not achieve normal vascular perfusion by the study end point of 120 minutes after administration of the drug.

TABLE 7

The Accumulated Change In Vascular Perfusion Volume Between 10 Minutes After The Vasospasm To 120 Minutes After The Application Of the Topical Composition (ml/min, N = 10 for each group)

| 0 μg $PGE_1$ (Blank Control) | 80 μg $PGE_1$ | 160 μg $PGE_1$ | 320 μg $PGE_1$ | 640 μg $PGE_1$ | 320 μg $PGE_1$ without DDAIP |
|---|---|---|---|---|---|
| 4595 ± 564 | 7590 ± 657 | 10960 ± 361 | 18550 ± 278 | 21753 ± 335 | 4356 ± 213 |

The accumulated vascular perfusion volume that occurred between 10 minutes after the vasospasm and 120 minutes after the application of the topical composition is presented in Table 7, above. The treatment with the blank control composition ("0 μg $PGE_1$") and the positive control, 0.4% $PGE_1$ topical composition without penetration enhancer produced small, comparable changes in vascular perfusion volume. Administration of topical compositions having higher amounts of $PGE_1$ produced a greater accumulated change in vascular perfusion volume and showed a dose-dependent increase.

TABLE 8

The Average Time Required To Return To The Initial Vascular Perfusion Volume (Minutes, N = 10 for each group)

| 0 μg $PGE_1$ (Blank Control) | 20 μg $PGE_1$ without DDAIP | 80 μg $PGE_1$ | 160 μg $PGE_1$ | 320 μg $PGE_1$ | 640 μg $PGE_1$ |
|---|---|---|---|---|---|
| 120 | 120 | 120 | 30 | 10 | 7 |

The average time required after administration of the topical composition to return to the initial vascular perfusion volume are presented in Table 8, above. The treatment with the blank control composition ("0 μg $PGE_1$"), 0.4% $PGE_1$ topical composition without penetration enhancer and a topical composition comprising 80 μg $PGE_1$ did not produce recovery of vascular perfusion volume within the 120 minute duration of the test. Administration of topical compositions having higher amounts of $PGE_1$ produced recovery of vascular perfusion volume and showed a dose-dependent decrease in the time required for recovery.

Ten to Ninety Minutes After Administration of the Drug:

Compared to blank control group, no significant differences (P>0.05) of vascular perfusion changes of positive control group was noticed, while significant differences (P<0.01) of vascular perfusion changes of other $PGE_1$ concentration groups were observed.

One Hundred and Twenty Minutes after Administration of the Drug:

Compared to blank control group, significantly different (P<0.01) vascular perfusion changes were observed for all of the $PGE_1$ concentration groups. Compared to 160 μg $PGE_1$ group, significantly different (P<0.01) vascular perfusion changes were observed for all of the $PGE_1$ concentration groups except positive control and 80 μg $PGE_1$ concentration groups (P<0.01).

The experimental results indicated topical application of $PGE_1$ sterile cream is an effective antagonist for adrenaline-induced vasospasm and vascular perfusion changes. A dose-dependent relationship was observed for $PGE_1$ in the concentration range of 80 μg to 640 μg.

Example 4

Pharmacodynamic Study of a Study of a Topical $PGE_1$ Composition as an Antagonist for Vasospasm During Surgical Operation in Rabbit The spasmolysis (reversal of vasospasm) and vasodilation effects of a topical $PGE_1$ composition (Composition H of Example 1 modified as appropriate to contain the indicated amount of $PGE_1$) on vasospasm induced by adrenaline hydrochloride were studied by monitoring vascular diameter changes in rabbit ears.

Rabbits were obtained and anesthetized as described in Example 2, above. A total of 70 rabbits were randomly assigned into 7 groups with 10 rabbits per group.

Blood flow velocity and vascular cross section area were measured and analyzed using a Toshiba Multifunction Ultrasonography 6000 system.

A portion of femoral artery about 2 cm long was exposed through a 3 cm incision. Four drops of adrenaline hydrochloride (1 mg/1 ml) were dropped by a 1 ml syringe onto the surface of center of the exposed segment of femoral artery to induce vasospasm. The entire test was performed under a constant room temperature of 20 degrees Celsius. About ten minutes after the application of adrenaline hydrochloride, the operating field was irrigated with sterile saline topically and dried with sterile pad. A single administration of 40 mg topical composition with various $PGE_1$ concentrations was applied onto the surface of the 2 cm portion of the isolated femoral artery. A single administration of four drops of papaverine (30 mg/ml) from a 1 ml syringe onto this field was used as a positive control.

The incision was closed after the application of the topical composition. The ultrasonic probe was put at a fixed location 1 cm from the incision. The values of the blood flow velocity and vascular cross sections were recorded by the Toshiba Multifunction Ultrasonography at time points of normal condition after anesthesia, 5 minutes and 10 minutes after vasospasm, 5 minutes, 10 minutes, 15 minutes, 30 minutes, 60 minutes, 90 minutes, and 120 minutes after administration of the drug. In general, blood flow volume=blood flow velocity× vascular cross section The data were expressed as average±SD; t-test was used for statistical analysis. The averaged data are reported in Table 9, below, as instantaneous blood flow volume±standard deviation (SD), N=10, and shown graphically in FIG. 6.

The accumulated blood flow volume that occurred between 10 minutes after the vasospasm and 120 minutes after the application of the topical composition is presented in Table 10, above. The treatment with the blank control composition

TABLE 9

The instantaneous blood flow volume changes before and after the drug administration ($mm^3/s$)

| Group N | 40 μg 10 | 80 μg 10 | 160 μg 10 | 320 μg 10 | 160 μg w/o DDAIP 10 | Papaverine 10 | Blank Control 10 |
|---|---|---|---|---|---|---|---|
| Normal Condition | 326 ± 14.40 | 318 ± 14.92 | 327 ± 13.22 | 321 ± 12.75 | 332 | 325 ± 9.80 | 330 ± 15.09 |
| 5 min after Vasospasm | 104 ± 5.64 | 105 ± 5.48 | 109 ± 4.74 | 107 ± 5.56 | 105 | 107 ± 4.11 | 108 ± 6.70 |
| 10 min after Vasospasm | 87 ± 5.66 | 86 ± 5.10 | 82 ± 4.14 | 87 ± 4.32 | 84 | 86 ± 4.76 | 84 ± 5.94 |
| 5 min after Drug | 206 ± 10.54 | 230 ± 11.16 | 816 ± 23.12 | 364 ± 14.92 | 142 | 319 ± 13.27 | 149 ± 8.68 |
| 10 min after Drug | 251 ± 15.36 | 292 ± 13.14 | 769 ± 24.97 | 254 ± 25.30 | 182 | 358 ± 13.95 | 132 ± 10.04 |
| 15 min after Drug | 289 ± 18.55 | 292 ± 12.45 | 654 ± 22.50 | 582 ± 24.58 | 247 | 402 ± 18.44 | 146 ± 8.43 |
| 30 min after Drug | 183 ± 13.86 | 413 ± 14.28 | 490 ± 16.29 | 649 ± 25.97 | 290 | 435 ± 17.76 | 197 ± 12.53 |
| 60 min after Drug | 214 ± 12.57 | 307 ± 12.06 | 462 ± 17.68 | 809 ± 27.46 | 256 | 296 ± 12.58 | 210 ± 16.44 |
| 90 min after Drug | 262 ± 13.56 | 290 ± 12.06 | 455 ± 12.61 | 562 ± 25.70 | 274 | 287 ± 11.96 | 254 ± 16.73 |
| 120 min after Drug | 287 ± 14.16 | 271 ± 10.89 | 451 ± 11.42 | 541 ± 23.06 | 279 | 274 ± 10.88 | 266 ± 18.29 |

Figure 6:
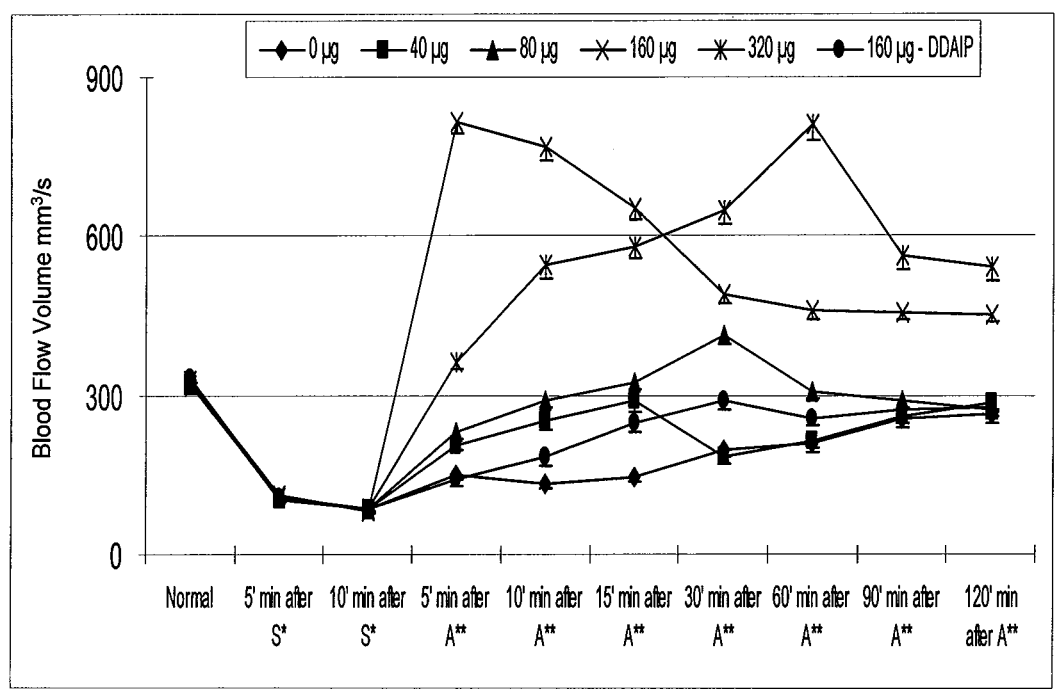
FIG. 6 is a graphical representation of the averaged results of a study of vascular perfusion volume in vasospasm in rabbit femoral artery as measured by ultrasonography. As noted above, a single administration of 40 mg of a topical composition with various $PGE_1$ concentrations was applied to the surface of a surgically exposed portion of a femoral artery, 10 minutes after the application of adrenaline hydrochloride. Administration of the topical composition comprising 0.1, 0.2, 0.4 or 0.8 weight percent $PGE_1$ provided respective doses of 80 (filled circles), 80 (filled triangles), 160 ("X") and 320 ("*") micrograms (μg) of $PGE_1$ as well as cream without $PGE_1$ (0 μg $PGE_1$, filled diamonds) and 160 μg $PGE_1$ topical composition without DDAIP (filled circles). Measurements were taken of the normal condition of the blood vessels after anesthesia, at 5 and 10 minutes after vasospasm was induced, and at 5, 10, 15, 30, 60, 90 and 120 minutes after the administration of the various $PGE_1$ compositions. Data are presented as mean±standard deviation. S* refers to the time of the vasospasm; A** refers to the time of the administration of topical composition.

FIG. 6 is a graphical representation of the averaged results of vascular perfusion volume in rabbit femoral artery as measured by ultrasonography. As noted above, a single administration of 40 mg of topical composition with various $PGE_1$ concentrations was applied to the surface of a surgically exposed portion of a femoral artery, 10 minutes after the application of adrenaline hydrochloride. Administration of the topical composition comprising 0.1, 0.2, 0.4 or 0.8 weight percent $PGE_1$ provided respective doses of 80 (filled circles), 80 (filled triangles), 160 ("X") and 320 ("*") micrograms (μg) of $PGE_1$ as well as cream without $PGE_1$ (0 μg $PGE_1$, filled diamonds), (0.4% $PGE_1$ topical composition without penetration enhancer, filled circles) and a positive control of 4 drops of 30 mg/ml papaverine. Measurements were taken of the normal condition of the blood vessels after anesthesia, at 5 and 10 minutes after vasospasm was induced, and at 5, 10, 15, 30, 60, 90 and 120 minutes after the administration of the various $PGE_1$ compositions. Data are presented as mean±standard deviation. S* refers to the time of the vasospasm; A** refers to the time of the administration of topical composition. The composition lacking the penetration enhancer DDAIP showed significantly lesser effect than the composition having the same dose of $PGE_1$ with DDAIP.

("0 μg $PGE_1$") and a composition comprising 40 μg $PGE_1$ produced small, comparable changes in vascular perfusion volume. Administration of papaverine produced a slightly greater effect that was comparable to that produced by composition comprising 80 μg $PGE_1$. Administration of topical compositions having higher amounts of $PGE_1$ produced a greater accumulated change in blood flow volume and showed a dose-dependent increase.

TABLE 11

The Average Time Required To Return To The Initial Blood Flow Volume (Minutes, N = 10 for each group)

| 0 μg $PGE_1$ (Blank Control) | 40 μg $PGE_1$ | 80 μg $PGE_1$ | 160 μg $PGE_1$ | 320 μg $PGE_1$ | Papaverine |
|---|---|---|---|---|---|
| 120 | 120 | 15 | 5 | 5 | 5 |

The average times required after administration of the topical composition to return to the initial blood flow volume are presented in Table 11, above. The treatment with the blank control composition ("0 μg $PGE_1$") and the 40 μg $PGE_1$ composition did not produce a recovery of blood flow volume within the 120 minute duration of the test. Administration of

TABLE 10

The accumulated blood flow volume ($cm^3$) from 10 minutes after vasospasm to 120 minutes after drug administration (N = 10 for each group)

| 0 μg $PGE_1$ (Blank Control) | 40 μg $PGE_1$ | 80 μg $PGE_1$ | 160 μg $PGE_1$ | 320 μg $PGE_1$ | Papaverine |
|---|---|---|---|---|---|
| 1525 ± 100.78 | 1686 ± 95.85 | 2243 ± 85.46 | 3598 ± 106.98 | 4466 ± 175.71 | 2341 ± 94.87 | topical compositions having higher amounts of $PGE_1$ produced recovery of blood flow volume as did papaverine.

At 10 to 90 Minutes After Administration of the Drug:

Compared to blank control group, significant differences ($P<0.01$) of instantaneous blood flow volume ($mm^3/s$) of all $PGE_1$ concentration groups were observed.

At 120 Minutes After Administration of the Drug:

Compared to blank control group, significant differences ($P<0.01$) of instantaneous blood flow volume ($mm^3/s$) of all $PGE_1$ concentration groups were observed except 40 μg, 80 μg, and positive control groups ($P>0.05$).

The experimental results indicated application of $PGE_1$ sterile cream directly to the exposed surface of a blood vessel could effectively counteract the adrenaline induced instantaneous blood flow volume changes and improve topical blood flow. The vascular dilation effect of $PGE_1$ sterile cream appears to be better than papaverine. A dose-dependent relationship was observed for $PGE_1$ between the concentration range of 80 μg to 320 μg.

Example 5

Result of Pilot Studies on Topical Applications of A Specially Formulated 0.4% $PGE_1$ Topical Composition The objects of these pilot studies were designed to explore the efficacy of a specially formulated 0.4 wt % $PGE_1$ topical composition for treating vasospasm and skin disorders that result from insufficient local blood circulation. Twenty four adult New Zealand rabbit, 3-4 kg, were divided into three groups: 12 rabbits were assigned into a Test Study Group; 6 rabbits were assigned into a $PGE_1$ Control Group and 6 rabbits were assigned into an Alcohol Control Group. One rabbit of each Group was selected to enter the study at the same time for each of the first six studies.

The rabbit's right ear was selected to be the test application site, while its left ear was observed as a control. An adrenaline solution (0.2 ml of a 0.1% (1:1000) solution) was injected into the area adjacent to both the central artery and vein near the bottom of both ears. Classic vasospasm appeared five minutes later on both ears. One of three test substances, 125 mg of a 0.4% $PGE_1$ topical composition containing 1.8% DDAIP HCl was applied to a 2 cm×2 cm area of skin adjacent to the central artery and vein of the right ear.

Vasospasm was induced in the same way in both ears of the rabbits of the $PGE_1$ Control Group and the Alcohol Control Group. Similarly, 1 mg of $PGE_1$ dissolved in 75% aqueous ethanol, or the 75% aqueous ethanol vehicle alone were applied to the right ears of the rabbits of the $PGE_1$ Control Group and the Alcohol Control Group respectively. The time course of changes in blood vessel diameter was observed.

In the Test Study Group, the vasospasm was alleviated five minutes after the 0.4 wt % $PGE_1$ topical composition was applied to the skin of the right ear. The vessels of the right ear were obviously dilated 15 minutes later. The vascular bed of the right ear was also dilated and reaching a maximum at 30 minutes after application. The blood flow of the right ear increased obviously. The effect lasted two hours then disappeared gradually. The vasospasm of the left ear alleviated spontaneously two hours later.

In the $PGE_1$ Control Group, the vasospasm was alleviated slightly 20 minutes after the application of $PGE_1$ onto the skin of the right ear. The vessels of the right ear were dilated 30 minutes later. The dilation effect lasted 60 minutes then disappeared. No significant remaining changes were observed of the vascular bed of the right ear. The vasospasm of the left ear lasted two hours then disappeared spontaneously. In the Alcohol Control Group, the vasospasm was alleviated slightly 10 minutes after the application of 75% Alcohol onto the skin of the right ear. The vasospasm disappeared 90 minutes later. No significant remaining changes were observed of the vascular bed of the right ear. The vasospasm of the left ear lasted two hours then disappeared automatically.

Example 6

Topical Application to Improve and Prevent Local Vasospasm During Surgery

The use of topical prostaglandin compositions during surgery for the prevention and treatment of local vasospasm was studied.

Approximately 125 mg of the topical prostaglandin composition H of Example 2 containing 0.4% $PGE_1$ (dose 0.5 mg $PGE_1$) was applied to the vascular extima at the anastomotic site when local vasospasm appeared during vascular anastomosis. The changes of local vascular and systemic hemodynamics before and after vasospasm were observed and recorded. Eleven subjects were assigned to three groups.

Group 1 consisted of six subjects who needed arteriovenous fistula repair due to renal failure and for whom systemic application of vasodilator was contraindicated due to several concomitant diseases. Approximately 125 mg of the topical prostaglandin composition was applied onto the vascular extima after shaping the arteriovenous fistula during arteriovenous anastomosis.

Group 2 contained two subjects who were emergency hand trauma patients, who had classic vasospasm right after the injury. Approximately 125 mg of the topical prostaglandin composition was applied onto the vascular extima at the anastomotic site after vascular anastomosis.

Group 3 consisted of three subjects who were vascular surgical patients. Vasospasm appeared in two subjects of Group 3 after vascular anastomosis performed when removing a clot. Vasospasm appeared in the other Group 3 subject after vascular anastomosis performed when removing vascular obliteration. Approximately 125 mg of the topical prostaglandin composition was applied onto the vascular extima at the anastomotic site after vascular anastomosis.

No other vasodilators were given to the patients after the surgery. Changes of local vascular diameter were recorded by macroscopy using a digital camera. Laser Doppler flowmetry was also used to measure local hemodynamic changes.

The topical prostaglandin composition was applied after classic vasospasm appeared after vascular anastomosis and lasting for more than 15 minutes without spontaneous alleviation. Typically, the vasospasm was alleviated 2-5 minutes after the application of the topical prostaglandin composition, and the blood vessel was obviously dilated after 10 minutes. The diameter of the blood vessel generally increased to about twice that seen during the vasospasm; while the arterial pulse appeared to be reinforced as well. The dilation effect continued and was also observed at twenty minutes following application. Local blood flow as measured by laser Doppler blood flowmetry showed a five-fold increase in maximum local blood flow compared to prior to application of the topical prostaglandin composition. No significant changes of blood pressure and pulse were noted. No secondary vasospasm was noted in any patient during the two-week observation period following surgery. The wound healing progressed satisfactorily.

While the foregoing is intended to be illustrative of the present invention, the scope is defined by the appended claims. Numerous variations and modifications may be effected without departing from the true spirit and scope of the invention.

We claim:

1. A method of improving microcirculation in a replanted body part in a subject needing such treatment comprising the step of:
applying directly to exposed tissues such as the vascular extima of blood vessels during surgery to reattach a severed body part or during wound treatment an effective amount of a semi-solid composition that comprises:
a prostaglandin selected from the group consisting of prostaglandin $E_1$, a pharmaceutically acceptable salt thereof, a $C_1$ to $C_4$ alkyl ester thereof and a mixture thereof;
a penetration enhancer selected from the group consisting of an alkyl-(N-substituted amino) ester elected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof;
a shear-thinning polymer thickener selected from the group consisting of a shear-thinning polysaccharide gum and a shear-thinning polyacrylic acid polymer;
a lipophilic component that is selected from the group consisting of an aliphatic $C_1$ to $C_8$ alcohol, an aliphatic $C_8$ to $C_{30}$ ester, a liquid polyol and a mixture thereof;
water and
a buffer system that provides a buffered pH value for said composition in the range of about 3 to about 7.4.

2. The method of claim 1 wherein the subject needs treatment of vasospasm occurring during or after microsurgery.

3. A method of improving local microcirculation in a tissue comprising:
applying directly to the surface of the affected tissue of a subject needing treatment to improve the microcirculation of that tissue an effective amount of a semi-solid composition, the composition comprising
a vasoactive prostaglandin selected from the group consisting of prostaglandin $E_1$, a pharmaceutically acceptable salt thereof, a $C_1$ to $C_4$ alkyl ester thereof and a mixture thereof;
a penetration enhancer selected from the group consisting of an alkyl-(N-substituted amino)ester elected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof;
shear-thinning polymer thickener selected from the group consisting of a shear-thinning polysaccharide gum and a shear-thinning polyacrylic acid polymer;
a lipophilic component that is selected from the group consisting of an aliphatic $C_1$ to $C_8$ alcohol, an aliphatic $C_8$ to $C_{30}$ ester, a liquid polyol and a mixture thereof;
water and a buffer system that provides a buffered pH value for said composition in the range of about 3 to about 7.4.

4. The method of claim 3 further comprising the step of applying the semi-solid composition to the vascular extima of the blood vessels supplying the tissue.

5. The method of claim 3 wherein the surface to which the composition is applied is the surface of the skin.

6. The method of claim 3 wherein the polysaccharide gum is a shear-thinning polysaccharide gum.

7. The method of claim 6 wherein the shear-thinning polysaccharide gum is a galactomannan gum or a modified galactomannan gum.

8. The method of claim 7 wherein the modified galactomannan gum is a modified guar gum.

9. The method of claim 3 wherein the shear-thinning polymer thickener is a shear-thinning polyacrylic acid polymer.

10. The method of claim 3 wherein the penetration enhancer is dodecyl 2-(N,N-dimethylamino)-propionate or a pharmaceutically acceptable salt thereof.

11. The method of claim 3 wherein the lipophilic component comprises at least one aliphatic $C_8$ to $C_{30}$ ester.

12. A method of eating reperfusion injury of an affected tissue comprising the steps of:
providing an effective amount of a semi-solid composition that comprises:
a vasoactive prostaglandin selected from the group consisting of prostaglandin $E_1$, a pharmaceutically acceptable salt thereof, a $C_1$ to $C_4$ alkyl ester thereof and a mixture thereof;
a penetration enhancer selected from the group consisting of an alkyl-(N-substituted amino) ester elected from the group consisting of an alkyl-(N-substituted amino)alkanoate, an alkyl-2-(N,N-disubstituted amino)alkanoate, an (N-substituted amino)alkanol alkanoate, an (N,N-disubstituted amino)alkanol alkanoate, a pharmaceutically acceptable salt thereof and a mixture thereof;
a shear-thinning polymer thickener selected from the group consisting of a shear-thinning polysaccharide gum and a shear-thinning polyacrylic acid polymer;
lipophilic component that is selected from the group consisting of an aliphatic $C_1$ to $C_8$ alcohol, an aliphatic $C_8$ to $C_{30}$ ester, a liquid polyol and a mixture thereof;
water and
a buffer system that provides a buffered pH value for said composition in the range of about 3 to about 7.4; and
applying the composition directly to the surface of the affected tissue of a subject needing treatment of reperfusion injury to that affected tissue.

13. The method of claim 12 further comprising the step of applying the composition directly to the vascular extima of blood vessels supplying the affected tissue.

* * * * *

UNITED STATES PATENT AND TRADEMARK OFFICE
CERTIFICATE OF CORRECTION

| | | |
|---|---|---|
| PATENT NO. | : 8,632,813 B2 | Page 1 of 1 |
| APPLICATION NO. | : 11/875725 | |
| DATED | : January 21, 2014 | |
| INVENTOR(S) | : Wen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1557 days.

Signed and Sealed this
Second Day of June, 2015

Michelle K. Lee
*Director of the United States Patent and Trademark Office*